(12) United States Patent
Rose et al.

(10) Patent No.: US 9,730,704 B2
(45) Date of Patent: *Aug. 15, 2017

(54) TOURNIQUET SYSTEM

(75) Inventors: Keith J. Rose, Corpus Christi, TX (US); Eric M. Yeates, Virginia Beach, VA (US); Mark D. Gantar, Coeur d'Alene, ID (US); Thomas M. Gregory, Belgrade, MT (US); Robert A. Kincaid, Bozeman, MT (US); Richard Siberell, Bozeman, MT (US); Clifton L. Cook, Boise, ID (US); Thomas A. Marx, Virginia Beach, VA (US); Brian Abrams, Spokane, WA (US)

(73) Assignee: SALANG, LLC, Corpus Christi, TX (US)

(*) Notice: Subject to any disclaimer, the term of this patent is extended or adjusted under 35 U.S.C. 154(b) by 817 days.

This patent is subject to a terminal disclaimer.

(21) Appl. No.: 12/733,337

(22) PCT Filed: Aug. 25, 2008
(Under 37 CFR 1.47)

(86) PCT No.: PCT/US2008/010053
§ 371 (c)(1),
(2), (4) Date: Feb. 23, 2011

(87) PCT Pub. No.: WO2009/029240
PCT Pub. Date: Mar. 5, 2009

(65) Prior Publication Data
US 2011/0270299 A1  Nov. 3, 2011

Related U.S. Application Data

(60) Provisional application No. 60/965,897, filed on Aug. 24, 2007.

(51) Int. Cl.
*A61B 17/00* (2006.01)
*A61B 17/132* (2006.01)
*A41D 1/08* (2006.01)

(52) U.S. Cl.
CPC ...... *A61B 17/1327* (2013.01); *A61B 17/1322* (2013.01); *A41D 1/08* (2013.01)

(58) Field of Classification Search
CPC .............. A61B 17/132; A61B 17/1322; A61B 17/1325; A61B 17/1327; A61B 17/135;
(Continued)

(56) References Cited

U.S. PATENT DOCUMENTS

| 35,038 | A | * | 4/1862 | Pierce | ............................ 606/203 |
| 268,407 | A | * | 12/1882 | Hughes | ................ A61B 17/132 |
|  |  |  |  |  | 24/115 H |

(Continued)

*Primary Examiner* — Melanie Tyson
*Assistant Examiner* — Erin Colello
(74) *Attorney, Agent, or Firm* — McAndrews, Held & Malloy, Ltd.

(57) ABSTRACT

A tourniquet system embedded within the garment, the tourniquet system including a band, an optional bar, and an anti-pinch plate. The bar comprises an elongate portion of material having a first end portion, an intermediate portion, and a second end portion, at least one aperture formed in the bar so as to accept the band and allow the band to pass therethrough, at least one locking protrusion that extends from at least one of the first end portion or the second end portion. The anti-pinch plate includes one or more band receiving apertures formed so as to accept the band and allow the band to pass therethrough, wherein the anti-pinch plate includes one or more locking notches formed substantially along an edge portion of the anti-pinch plate, wherein the locking notches provide a means for securing at least a portion of the bar to the anti-pinch plate.

20 Claims, 21 Drawing Sheets

(58) Field of Classification Search
CPC ..... A61B 17/12; A61B 5/022; A61B 5/02233; A61B 5/02241; A44B 11/12; Y10T 24/1498; Y10T 24/13; A61F 5/30; A61F 5/32; A61F 5/34; A61F 2013/00106; A61F 2013/00174; A61F 2013/0028; A61F 2013/00468; A61F 2013/00463; A61F 13/08; A61F 5/012; A61H 9/005; A61H 9/0078; A41D 1/08
USPC ....... 606/201–203; 2/911; 24/157, 185, 200; 602/53, 75, 58

See application file for complete search history.

(56) References Cited

U.S. PATENT DOCUMENTS

| | | | | |
|---|---|---|---|---|
| 947,284 A * | 1/1910 | Sourek | ............. | A44B 11/12 24/170 |
| 1,566,235 A * | 12/1925 | Sheehan | ............. | 606/203 |
| 1,743,452 A * | 1/1930 | Hatch | ............. | A61B 17/1327 606/203 |
| 2,084,412 A * | 6/1937 | Schaefer | ............. | A41F 15/00 24/186 |
| 2,113,534 A * | 4/1938 | Brown | ............. | A61B 17/1327 606/203 |
| 2,152,922 A * | 4/1939 | Robinson | ............. | 606/203 |
| 2,387,428 A * | 10/1945 | Brothers | ............. | A61B 17/1327 606/203 |
| 2,480,430 A * | 8/1949 | Walters | ............. | A61B 17/1325 606/203 |
| 2,518,921 A * | 8/1950 | Middaugh | ............. | A61B 17/1327 24/129 R |
| 2,702,551 A * | 2/1955 | Hobson | ............. | A61B 17/1322 606/203 |
| 2,754,825 A * | 7/1956 | Richmond | ............. | A61B 17/1327 606/203 |
| 2,893,394 A * | 7/1959 | Thomsen | ............. | A61B 17/1327 24/200 |
| 3,969,772 A * | 7/1976 | Pravaz | ............. | 2/79 |
| 4,273,130 A * | 6/1981 | Simpson | ............. | 606/203 |
| 5,628,723 A * | 5/1997 | Grau | ............. | A61B 17/1325 602/53 |
| 6,477,710 B1 * | 11/2002 | Ojoyeyi | ............. | 2/69 |
| 6,852,089 B2 * | 2/2005 | Kloecker et al. | ............. | 602/75 |
| 6,884,254 B2 * | 4/2005 | Brooks | ............. | A61B 17/1327 24/71 R |
| 6,899,720 B1 * | 5/2005 | McMillan | ............. | A61B 17/1322 606/203 |
| 6,960,223 B1 * | 11/2005 | Ambach | ............. | A61B 17/1327 606/203 |
| 7,530,990 B2 * | 5/2009 | Perriello et al. | ............. | 606/232 |
| 7,604,651 B1 * | 10/2009 | Harris et al. | ............. | 606/203 |
| 7,842,067 B2 * | 11/2010 | Esposito | ............. | A61B 17/1327 606/203 |
| 7,892,253 B2 * | 2/2011 | Esposito | ............. | A61B 17/1327 606/203 |
| 8,348,970 B2 * | 1/2013 | Janota | ............. | 606/203 |
| 2003/0028215 A1 * | 2/2003 | Brooks | ............. | 606/203 |
| 2003/0139766 A1 * | 7/2003 | McEwen | ............. | A61B 17/135 606/203 |
| 2005/0049630 A1 * | 3/2005 | Ambach | ............. | A61B 17/1327 606/203 |
| 2005/0240217 A1 * | 10/2005 | Jennifer et al. | ............. | 606/203 |
| 2005/0273134 A1 * | 12/2005 | Esposito | ............. | A61B 17/1327 606/203 |
| 2007/0005107 A1 * | 1/2007 | Janota | ............. | A61B 17/1322 606/203 |
| 2007/0038243 A1 * | 2/2007 | Rutherford | ............. | A61B 17/1322 606/203 |
| 2007/0299467 A1 * | 12/2007 | Arias | ............. | A61B 17/1322 606/203 |
| 2008/0183207 A1 * | 7/2008 | Horne | ............. | A61B 17/1327 606/203 |
| 2009/0024159 A1 * | 1/2009 | Nee | ............. | A61B 17/1327 606/203 |
| 2009/0062842 A1 * | 3/2009 | Esposito | ............. | A61B 17/1327 606/203 |

* cited by examiner

TOURNIQUET SYSTEM

CROSS-REFERENCE TO RELATED APPLICATIONS

This is a Continuation of U.S. Patent Application No. 60/965,897, filed Aug. 23, 2007, the disclosure of which is incorporated herein by reference.

BACKGROUND OF THE INVENTION

1. Field of the Invention

This invention relates generally to tourniquets. In particular, the present invention relates to a tourniquet system having a tourniquet band and an anti-pinch plate. The present invention also relates to various garments that may be used in conjunction with the tourniquet system.

2. Description of Related Art

A tourniquet is generally a tightly tied band applied around a body part (for example, a bandage tightened around an arm or a leg by twisting) in an attempt to arrest bleeding by forcibly compressing a blood vessel. A tourniquet is typically applied as a last resort method when bleeding cannot be controlled through alternative methods and the amount of blood loss is likely to cause death in seconds to minutes.

Because the application of a tourniquet stops the flow of blood to the portion of the limb below the level where the tourniquet is applied, the resulting anoxia can cause the death of at least a portion of the limb, often requiring the later surgical amputation of the limb just below the level the tourniquet is applied. This is likely to occur when the tourniquet stays in place several hours.

The decision to employ a tourniquet should be made by an emergency medical technician or preferably a doctor if at all possible. However, when severe external bleeding cannot be controlled by other means, and a tourniquet may be the only way to save the life of an injured individual, time constraints might require the decision to be made by the injured party himself.

On the modern battlefield, for example, life-threatening bleeding from injuries to extremities is more common because modern body armor tends to protect the torso from such wounds. Blast injuries to limbs rarely result in a clean amputation or a salvageable limb, and rapid application of a tourniquet can be lifesaving when arterial bleeding results from such a major injury.

It is believed that approximately 70% of all preventable fatalities on the modern battlefield are the result of extremity trauma. Unfortunately, medical care is not always immediately available and an injured individual or someone within close proximity has to tend to their own or their friend's wounds. This has been particularly true where use of improvised explosive devices has sharply increased. The users have armor that protects their torsos and to a lesser degree their heads; however, since the extremities are left unprotected the users are more likely to suffer a severe laceration in those extremities. The large loss of blood from these lacerations can be avoided with the quick application of a well-placed tourniquet.

It has been noted that tourniquets are used far more frequently in combat injury situations. Therefore, most military personnel are now required to carry a tourniquet as part of their individual first aid kits, and first aid training for soldiers now typically addresses the "prompt and decisive" use of tourniquets to control life-threatening extremity bleeding.

SUMMARY OF THE INVENTION

However, known tourniquets merely include a band and a bar. When the tourniquet is applied, the band is positioned around an injured arm or leg, at a position above the injury. Once the band is in position, a separate bar is placed between the band and the extremity and the bar is rotated. As the bar is rotated, the band is twisted, thereby reducing the circumference of the band and tightening the band so as to forcibly compress the extremity (and the blood vessels within the extremity) and reduce or eliminate blood flow below the level where the tourniquet is applied.

Additionally, because of the degree of personalization that occurs within each individual soldier's kits, a carried tourniquet's location on a soldier can vary greatly from individual to individual causing a fellow soldier or attending Medical Aide to take even more time in the complete application cycle or effort.

In some instances, a carried tourniquet can become separated from the injured soldier causing him, her, or an attending Medical Aide to again spend time in locating it rather than in applying it.

In certain situations, the injured, weakened, user may have to apply the tourniquet himself or herself. Unfortunately, particularly in a stressful situation, it may be difficult to locate, apply, properly position, or effectively utilize a tourniquet.

Additionally, known tourniquets are often carried in the field by someone else, such as a dedicated Medical Aide, or by the potential user in a pouch or pack. The time lost in accessing the tourniquet and/or positioning it could be life threatening. In some cases, the injury and/or the position of the wounded individual might prevent the tourniquet from being accessed and positioned at all.

Unfortunately, when the band of a known tourniquet is twisted, material, such as the user's skin (if the tourniquet is applied over bare skin) or garment fabric (if the tourniquet is applied over a garment), tends to bunch up and/or be twisted into the band as the tourniquet is tightened. Wadded clothing can prevent a tourniquet from obtaining adequate pressure to stop blood flow and additional damage can be done to the user if skin is twisted into the band.

Thus, the present invention relates generally to tourniquets. In particular, the present invention relates to a tourniquet system having a tourniquet band and an anti-pinch plate. In various exemplary embodiments, the present invention also relates to various garments that may be used in conjunction with the tourniquet system.

According to various aspects of the present invention, in various exemplary embodiments, the invention includes an anti-pinch plate that allows the tourniquet band to be tightened without the risk of twisting material (skin, the tourniquet webbing, and/or fabric) into the band.

In various exemplary, nonlimiting embodiments, the tourniquet system of the present invention includes a bar that is an integral component of the tourniquet system.

In various exemplary embodiments, the present invention alleviates certain of the drawbacks described above with respect to the current methods and systems for dealing with severe lacerations and incorporates several additional beneficial features.

While the tourniquet system of the present invention may be designed to function as a stand-alone system, in various exemplary, nonlimiting embodiments, the tourniquet system of the present invention may be incorporated into or included as an integral component of a garment. In these exemplary embodiments, the tourniquet system of the present invention may be incorporated into a more traditional garment, such as, for example, a pair of pants, a shirt, or a jacket. Additionally, the tourniquet system may also be incorporated into other traditional or non-traditional garment, such as, for example, a harness, body-fitting framework, suspension system, Long John type configuration, bicycle type or exercise shorts, compression short or shirt, wetsuits, sky diving garments, hazmat suits, pressurized suits, flight suits, hunting apparel, overalls, coveralls, specialized uniforms or suits, protective coverings worn over conventional clothing, and/or any other garment, quasi-garment, or article of clothing that is capable of maintaining one or more tourniquets in a relatively fixed position relative to the body of a wearer.

For example, the tourniquet system of the present invention may be incorporated into wetsuits for implementation after shark attacks, sky diving garments to be worn by individuals being dropped into an area not easily accessible by ground, or hazmat suits where the user might be in contaminated conditions that cannot be readily entered by supporting trauma personnel.

In various exemplary, nonlimiting embodiments the tourniquet system may also include an attached transmitter that would activate when the tourniquet system is used to send an alert including, for example, information regarding the user's location and for identifying the particular tourniquet system employed.

It should be appreciated that alternate embodiments may include, for example, a pneumatic tourniquet that a wearer can trigger to apply increasing compressing pressure at a desired tourniquet location without any manual force.

In certain additional exemplary embodiments, the tourniquet system of the present invention allows for utilization of layered garments, where in each layered garment allows access to one or more embedded tourniquets.

In various exemplary, nonlimiting embodiments, the present invention provides a much-needed medical supply to each user without sacrificing the comfort of the user, the weight of the user's garment, or the user's ability to move through and interact with the environment.

In various exemplary, nonlimiting embodiments, the present invention places one or more tourniquets in particular locations, such that a reduced amount of pressure may be required to arrest the large amount of blood flow In certain exemplary, nonlimiting embodiments, the tourniquet system of the present invention is positioned integral to a garment such that the tourniquet system can be in approximate position for use.

Thus, the inclusion of the anti-pinch plate increases stability of the tourniquet system when in use, allows for better total compression across a wider area of application, and acts to limit focal tissue damage. This can result in a reduction of the pain caused by applying the tourniquet system when compared to known tourniquets systems. It can also limit pain in regard to skin being trapped by the system and the skin and the wadded clothing or the tourniquet webbing, being trapped by the system.

In certain exemplary, nonlimiting embodiments, the tourniquet system of the present invention includes a band having a first end portion and a second end portion, a bar, wherein the bar comprises an elongate portion of material having a first end portion, an intermediate portion, and a second end portion, at least one band receiving aperture formed in the bar so as to accept the band and allow the band to pass therethrough, at least one locking protrusion that extends from at least one of the first end portion or the second end portion, and an anti-pinch plate, wherein the anti-pinch plate includes one or more band receiving apertures formed so as to accept the band and allow the band to pass therethrough, wherein the anti-pinch plate includes one or more locking notches formed substantially along an edge portion of the anti-pinch plate, wherein the locking notches provide a means for securing at least a portion of the bar to the anti-pinch plate. Portions of the band pass through the one or more band receiving apertures, thereby maintaining the position of the band relative to the anti-pinch plate, and wherein the first end portion passes through at least one aperture formed in the bar and the second end portion passes through at least one aperture formed in the bar, and wherein the anti-pinch plate is positioned beneath the bar to limit or prevent material from being twisted into the band as the band is tightened by the rotation of the bar. The at least one tourniquet system is embedded within the garment such that at least a portion of the band of the at least one embedded tourniquet system is maintained within a channel formed in at least a portion of an inner surface of the garment such that the tourniquet system is maintained in a desired location relative to the garment and/or a body of a wearer.

Accordingly, this invention provides a tourniquet system of improved design.

This invention separately provides a tourniquet system, having an improved tightening and securing mechanism.

This invention separately provides a tourniquet system, having an anti-pinch plate.

This invention separately provides a tourniquet system, which allows for one handed operation and manipulation.

This invention separately provides a tourniquet system, which may be easily applied and/or engaged and disengaged.

This invention separately provides a tourniquet system, the application of which is easily reversible.

This invention separately provides a relatively low bulk tourniquet system, which has little weight and a relatively flat-to-the-body profile.

This invention separately provides a tourniquet system, which can be easily utilized in the field.

This invention separately provides a tourniquet system, which is compact enough to allow a user to easily carry extra tourniquet systems.

This invention separately provides a tourniquet system, which may be carried "in place" on the body of the user.

This invention separately provides a tourniquet system, which potentially allows for a plurality of devices per limb; each one better located to save the greatest amount of the extremity.

This invention separately provides a tourniquet system, which allows for use on a "trapped" or inaccessible limb.

This invention separately provides a tourniquet system, which can be retrofitted to an existing garment.

This invention separately provides a garment or set of garments, which provide easier access use to the tourniquet system(s) by the wearer or medic.

This invention separately provides a tourniquet system, which is capable of creating and maintaining pressure on a limb and not the garment where pressure could be blocked by, for example, items carried in the garment pockets or, in some cases, even the garment material.

This invention separately provides a garment, which is capable of having one or more embedded tourniquet systems.

This invention separately provides a garment, which is capable of having one or more embedded tourniquet systems incorporated at strategic locations relative to the extremities of the wearer.

This invention separately provides a garment, which is capable of having one or more embedded tourniquet systems embedded into the inner surface of the garment.

This invention separately provides a garment, which is capable of having one or more embedded tourniquet systems embedded into the outer surface of the garment.

This invention separately provides a garment, which is capable of having one or more embedded tourniquet systems contained within garment.

This invention separately provides a garment, which provides access to each tourniquet's tightening and securing mechanism.

These and other features and advantages of this invention are described in or are apparent from the following detailed description of the exemplary, nonlimiting embodiments.

BRIEF DESCRIPTION OF THE DRAWINGS

The exemplary embodiments of this invention will be described in detail, with reference to the following figures, wherein like reference numerals refer to like parts throughout the several views, and wherein.

DETAILED DESCRIPTION OF EXEMPLARY EMBODIMENTS

For simplicity and clarification, the design factors and operating principles of the tourniquet system and/or tourniquet-supporting garment according to this invention are explained with reference to various exemplary embodiments of a tourniquet system and/or tourniquet-supporting garment. The basic explanation of the design factors and operating principles of the tourniquet system and/or the tourniquet-supporting garment is applicable for the understanding, design, and operation of the tourniquet system and/or the tourniquet-supporting garment of this invention.

It should also be appreciated that, as used herein, the term "garment" is used for basic explanation and understanding of the operation of the systems, methods, and apparatuses of this invention. Therefore, the term "garment" is not to be construed as limiting the systems, methods, and apparatuses of this invention. Thus, the term "garment" is to be understood to broadly include any complete or partial article of clothing that is capable of maintaining one or more tourniquets in a relatively fixed position relative to the body of a wearer. For example, the term "garment" is to be understood to broadly include any shirt, pants, jacket, harness, body-fitting framework, suspension system, Long John type configuration, bicycle type or exercise short, compression short or shirt, wetsuit, sky diving garment, hazmat suit, pressurized suit, flight suit, hunting apparel, overalls, coveralls, specialized uniform or suit, protective covering, and/or any other traditional or non-traditional garment, quasi- garment, or the like.

Likewise, it should also be appreciated that while the tourniquet supporting garment described herein is described as incorporating the tourniquet system of the present invention, the tourniquets supporting garment of the present invention may incorporate and allow utilization of any known or later developed tourniquet or tourniquet system.

While the attached drawing figures illustrate an exemplary tourniquet system integral to a pair of pants and a shirt, it should be appreciated that the tourniquet system may be utilized alone or in conjunction with any garment, as provided for herein. Likewise, it should be appreciated that any known or later developed tourniquet system may be utilized in conjunction with the pants or shirt illustrated in the attached drawing figures or any other garment incorporating the features of the present invention. Thus, it should be understood that the tourniquet system, pants, and shirt illustrated herein are merely for exemplary purposes and the tourniquet system and/or garments could be of other types.

Figure 1:
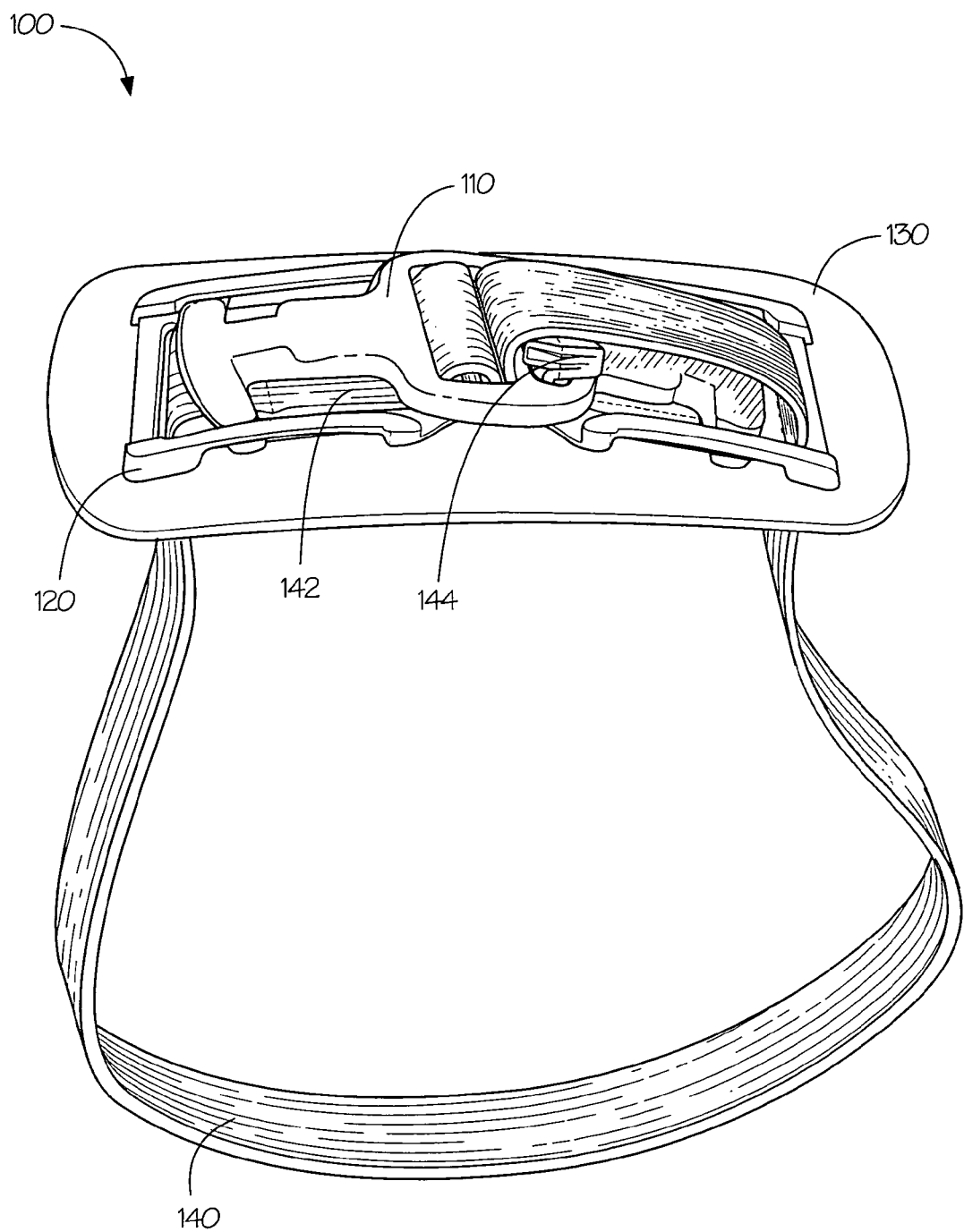
FIG. 1 shows a perspective view of a first exemplary embodiment of a tourniquet system according to this invention.
Figure 2A:
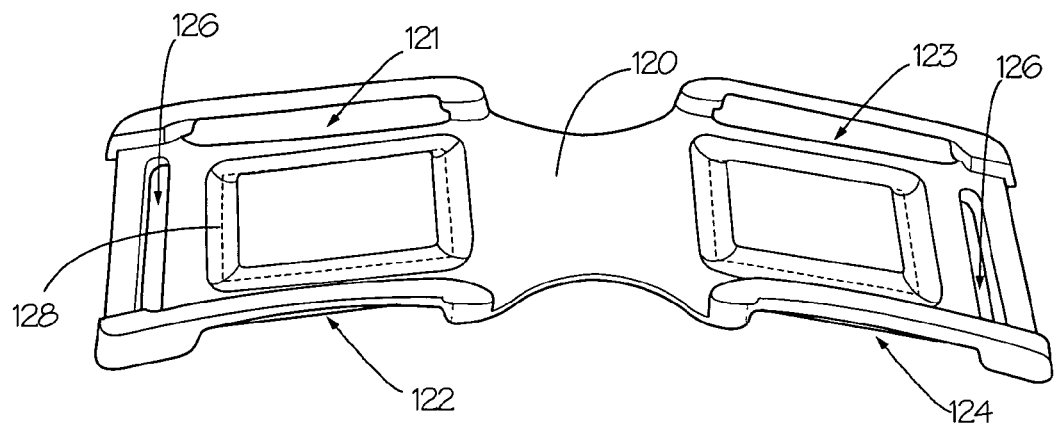
FIG. 2A shows a perspective view of a first exemplary embodiment of an anti-pinch plate.
Figure 2B:
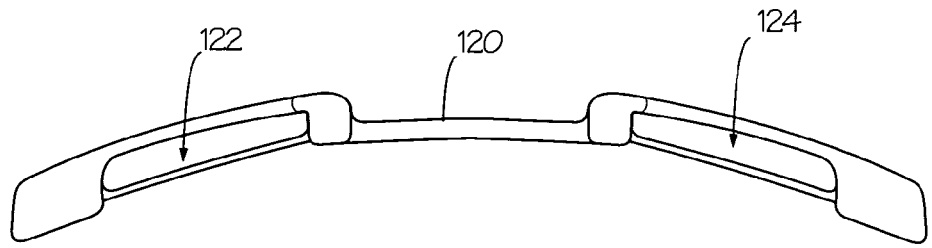
FIG. 2B shows a side view of a first exemplary embodiment of an anti-pinch plate.
Figure 3:
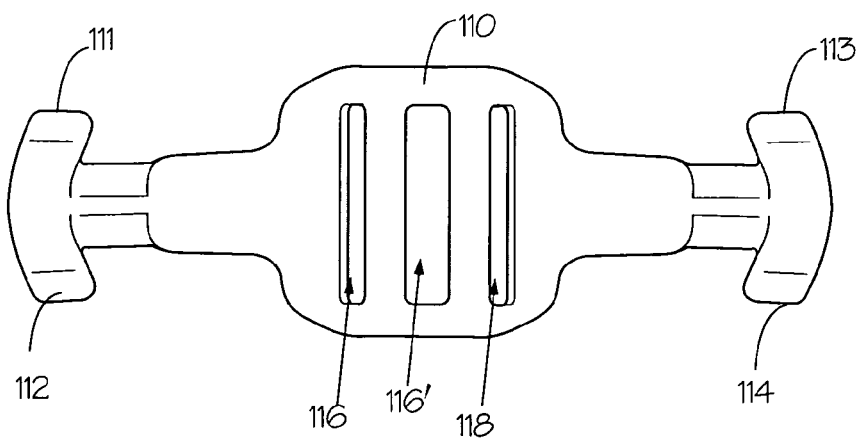
FIG. 3 shows a top view of a first exemplary embodiment of bar according to this invention.

Turning now to the drawing figures, FIG. 1 shows a perspective view of a first exemplary embodiment of a tourniquet system according to this invention, FIGS. 2A and 2B show a perspective view and a side view, respectively, of a first exemplary embodiment of an anti-pinch plate, and FIG. 3 shows a top view of a first exemplary embodiment of bar according to this invention.

As shown in FIGS. 1-3, the tourniquet system 100 includes at least some of a bar 110, an anti-pinch plate 120, and a band 140.

In various exemplary embodiments, the band 140 comprises a portion of substantially flat webbing or other material having a first end portion 142 and a second end portion 144. In various exemplary embodiments, one or both of the ends of the band 140 is/are formed so as to prevent the band 140 from being inadvertently removed from the apertures 116, 116', and/or 118 of the bar 110.

While the width of the band 140 will, in many embodiments, be approximately 1 inch or greater, it should be appreciated that the band 140 may be formed of any suitable width. In considering the width of the band 140, it should be appreciated that if the width of the band 140 is too narrow, the beneficial effect of the desired contact surface between the band 140 and the user's skin will be reduced. Additionally, if the width of the band 140 is too narrow, serious and/or permanent tissue damage could result, potentially forcing the amputation of a limb to which the tourniquet system 100 is applied at the location where the tourniquet system 100 is applied.

If the width of the band 140 is too wide, the band 140 may be impractical in light of the convenience of the design and the functionality that is desired in regard to the amount of pressure that can be applied to an extremity by the band 140.

In certain exemplary embodiments, the band 140 may be formed of a material having a substantially round, oval, or other cross-sectional shape. Furthermore, the band 140 may be formed of a tubular or solid material that may be substantially rigid and non-elastic or that may be somewhat elastic along a portion of the band 140 or the entire length of the band 140.

The length of the band 140 is at least sufficient to allow the band 140 to be positioned around the outer circumference of a desired extremity and to engage the bar 110. In various exemplary embodiments, additional length is included in the band 140, such that the band 140 may be incorporated into or easily wrap around a garment without restricting a wearer's freedom of movement when the tourniquet system is not employed.

The bar 110 comprises an elongate portion of material having a first end portion, an intermediate portion, and a second end portion. In various exemplary embodiments, the bar 110 includes one or more apertures 116, 116', and/or 118 formed in the intermediate portion (as illustrated) or proximate an end portion of the bar 110. The overall size and shape of the apertures 116, 116', and/or 118 is generally dictated by the size and shape of the tourniquet band 140. The apertures 116, 116', and/or 118 should be sufficient to allow the tourniquet band 140 to be accepted and pass through. In certain exemplary embodiments, the apertures 116, 116', and/or 118 are of a sufficient size and shape to allow the tourniquet band 140 to be accepted and pass through without significant resistance.

In various exemplary embodiments, the bar 110 includes one or more locking protrusions that extend from at least one of the first end portion or the second end portion. In various exemplary embodiments, the locking protrusions comprise substantially "T" shaped extensions that extend from at least one of the first end portion or the second end portion. As illustrated, the bar 110 may include substantially "T" shaped extensions 111, 112, 113, and 114 at each of the first end and the second end, respectively.

The "T" shaped extension(s) 111, 112, 113, and/or 114 allow the bar 110 to be more easily secured in position by a locking notch 121, 122, 123, or 124 of the anti-pinch plate 120, when the bar 110 has been turned such that the band 140 has been twisted and pressure applied by the band 140 (as described below). In this manner, once an appropriate amount of pressure has been applied by the tourniquet system 100, the bar 110 can be held in position by the interaction of at least one of the "T" shaped extension(s) 111, 112, 113, or 114 and a locking notch 121, 122, 123, or 124 of the anti-pinch plate 120.

In various other exemplary, nonlimiting embodiments, the "T" shaped extension(s) 111, 112, 113, or 114 of the bar 110 may be replaced or supplemented by at least one cross cut, or locking indention (not shown) formed proximate the first end portion or the second end portion. Each optionally included locking indention, is shaped so as to allow at least a portion of a locking notch 121, 122, 123, or 124 to be received within the indention, such that the bar 110 may be secured in position when the bar 110 has been turned such that the band 140 has been twisted and pressure applied by the band 140. In this manner, once an appropriate amount of pressure has been applied by the tourniquet system, the bar 110 can be held in position by the interaction of a locking indention and a locking notch 121, 122, 123, or 124 of the anti-pinch plate 120.

In various exemplary embodiments, the bar 110 is formed of a rigid or a semi-rigid plastic or polymeric material, such as a polymeric composite. In various exemplary embodiments, the bar 110 is injection-molded. Alternatively, the bar 110 may be heat-formed from sheet stock, such as, for example a polymer. In still other exemplary embodiments, the bar 110 may be stamped or rolled from a sheet of metal or may be formed from aluminum, titanium, and/or other metals, as well as various alloys and composites thereof, glass-hardened polymers, polymer or fiber reinforced metals, carbon fiber or glass fiber composites, continuous fibers in combination with thermoset and thermoplastic resins, chopped glass or carbon fibers used for injection molding compounds, laminate glass or carbon fiber, epoxy laminates, woven glass fiber laminates, impregnate fibers, polyester resins, epoxy resins, phenolic resins, polyimide resins, cyanate resins, high-strength plastics, nylon, glass or polymer fiber reinforced plastics, thermoform and/or thermoset sheet materials, and/or various combinations of the foregoing. It should also be appreciated that the bar 110 may be formed of, over-molded, or coated by multiple materials. Thus, it should be understood that the material or materials used to form the bar 110 is a design choice based on the desired appearance, flexibility, and functionality of the bar 110.

The edges and contours of the bar 110 may be shaped to minimize any damage to the user or a garment within which the tourniquet system 100 is utilized. In various exemplary embodiments, the bar 110 is curved over its length. In this manner, when the tourniquet system is not in use, the bar may be positioned such that the curvature of the bar 110 somewhat follows the curvature of the anti-pinch plate 120 and the curvature of the anti-pinch plate 120 somewhat follows the curvature of an extremity were the tourniquet system 100 will be used.

When the tourniquet system is in use, the orientation of the bar 110 is altered such that the curvature of the bar 110 tends to curve the bar 110 away from the curvature of the extremity where the bar 110 is positioned, thus allowing the bar 110 to not interfere with the limb when used and to be more easily manipulated by the operator. Alternatively, the bar 110 may be substantially planar over its length.

In various exemplary embodiments, the bar 110 may include one or more additional apertures to allow use of the bar 110 in conjunction with an additional bar or other mechanism that aids the user in operating the tourniquet system 100. In various exemplary embodiments, the bar 110 may include of provide for one or more raised or other surface preparations, a knob, wheel, handle, or other fixed or foldable extension that aids in the manipulation of the bar 110.

As further illustrated, the anti-pinch plate 120 is positioned beneath the bar 110 and acts to limit or prevent any material, such as, for example, the user's skin, the tourniquet webbing, and/or garment fabric, from bunching up or being twisted into the band 140 as the band 140 is tightened. Wadded clothing can also prevent a tourniquet from obtaining adequate pressure to stop blood flow.

In various exemplary embodiments, the anti-pinch plate 120 is formed of an elongate piece of material and is formed so as to be larger than the bar 110. However, it should be appreciated that the size and shape of the anti-pinch plate 120 is a design choice based on the desired appearance, flexibility, and functionality of the anti-pinch plate 120.

In various exemplary embodiments, the anti-pinch plate 120 is formed of a flexible material, such as a piece of web material or rubber, a relatively stable (inflexible) piece of fabric, or a piece of semi-flexible rubber or plastic sheet stock. Alternatively, the anti-pinch plate 120 may be formed of a rigid or a semi-rigid plastic, synthetic, or polymeric material, such as a polymeric composite. In various exemplary embodiments, the anti-pinch plate 120 is injection-molded. Alternatively, the anti-pinch plate 120 may be heat-formed from sheet stock, such as, for example a polymer. In still other exemplary embodiments, the anti-pinch plate 120 may be stamped or rolled from a sheet of metal or may be formed from aluminum, titanium, and/or other metals, as well as various alloys and composites thereof, glass-hardened polymers, polymer or fiber reinforced metals, carbon fiber or glass fiber composites, continuous fibers in combination with thermoset and thermoplastic resins, chopped glass or carbon fibers used for injection molding compounds, laminate glass or carbon fiber, epoxy laminates, woven glass fiber laminates, impregnate fibers, polyester resins, epoxy resins, phenolic resins, polyimide resins, cyanate resins, high-strength plastics, nylon, glass or polymer fiber reinforced plastics, thermoform and/or thermoset sheet materials, and/or various combinations of the foregoing. It should also be appreciated that the anti-pinch plate 120 may be formed of, over-molded, or coated by multiple materials. Thus, it should be understood that the material or materials used to form the anti-pinch plate 120 is a design choice based on the desired appearance, flexibility, and functionality of the anti-pinch plate 120.

In various exemplary embodiments, the anti-pinch plate 120 includes one or more locking notches 121, 122, 123, and/or 124, generally formed along a portion of an edge of the anti-pinch plate 120. The locking notches 121, 122, 123, and/or 124 provide a means for trapping or securing the bar 110, as described and shown herein. The locking notches 121, 122, 123, and/or 124 may comprise, for example, a raised or notched portion of the anti-pinch plate 120. It should be appreciated that the locking notches 121, 122, 123, and/or 124 may also include any appropriate notch, hole, aperture, loop, or other element capable of securing, trapping, or holding a portion of the bar 110. In various exemplary embodiments, the locking notches 121, 122, 123, and/or 124 may comprise a cord or other substantially elastic or non-elastic cord or banding material that is attached or coupled to the anti-pinch plate 120.

In certain exemplary embodiments, one or more of the bar locking indentions or "T" extensions 111, 112, 113, and/or 114 may be locked into position along an appropriate edge, notch, hole, aperture, loop, or other element of the anti-pinch plate 120 (as described below).

As with the bar 110, the edges and contours of the anti-pinch plate 120 may be shaped to minimize any damage to the user or a garment.

In various exemplary embodiments, the "T" shaped extension(s) 111, 112, 113, and/or 114 are formed so as to allow the bar 110 to be releasably secured to or within the anti-pinch plate 120, via the locking notch 121, 122, 123, and 124, when the tourniquet system 100 is not in use. Alternatively, the anti-pinch plate 120 may comprise a molded component formed so as to allow the bar 110 to be releasably secured to or within the anti-pinch plate 120, when the tourniquet system 100 is not in use.

The anti-pinch plate 120 also includes one or more band receiving apertures 126 that are shaped so as to accept the band 140 and allow the band 140 to pass through. The band receiving apertures 126 allow the anti-pinch plate 120 to be maintained in relative position to the band 140, particularly during use of the tourniquet system 100.

In various exemplary embodiments, when the tourniquet system 100 is not in use, the bar 110 may be releasably secured or attached to the anti-pinch plate 120 via the interaction of the "T" extensions 111, 112, 113, and 114 and the locking notches 121, 122, 123, and 124 of the anti-pinch plate 120. Alternatively, the bar 110 may be releasably secured or attached to the anti-pinch plate 120 via a releasable coupling means, such as, for example, one or more male/female snap-release buckles, one or more buttons, snaps, or other fastening, closure, a hook and loop fastener, such as Velcro, or any known or later developed releasable attachment means.

In various exemplary embodiments, the anti-pinch plate 120 may optionally include a stitchable portion 128 to aid in the stitchable attachment of the anti-pinch plate 120. The stitchable portion 128 may include for example, a portion of the anti-pinch plate 120 having a reduced thickness, so as to allow easier puncture of the anti-pinch plate 120 for stitching.

In various exemplary embodiments, both ends of the band 140 extend through or around the anti-pinch plate 120. One end of the band 140 is secured to the intermediate portion of the bar 110. The other end of the band 140 may, in various exemplary embodiments, also be secured to the intermediate portion of the bar 110. Alternatively, the other end of the band 140 may be passed through certain apertures 116, 116', and/or 118 of the bar 110 such that the band 140 can be tightened when a free end of the band 140 is pulled.

Depending on the geometry of the apertures employed, the apertures 116, 116', and/or 118 may secure the band 140, such that after the band 140 is pulled a certain length, the aperture(s) secure the band 140 so that the band 140 is held in place and can be grasped and pulled again. Thereby, allowing the band 140 to be effectively tightened in steps or stages, rather than requiring a single, long pull that may be beyond the capacity of the operator at the time.

The geometry of the apertures 116, 116', and/or 118 and the manipulation of the bar 110, allows the bar 110 to be pulled in one direction and the band 140 to be pulled in another, thereby allowing the band 140 to be adjusted in stages, rather than in a single, relatively long pull, such that the band 140 may be adjusted in confined or restricted environments.

As further illustrated in FIG. 1, the tourniquet system 100 may also include an optional pad 130. In various exemplary embodiments, the optional pad 130 may comprise a fabric, rubber, or rubberized material, such as, for example, neoprene. If included, the optional pad 130 is located below the anti-pinch plate 120 (inside the band 140) so as to provide an additional level of cushioning between the anti-pinch plate 120 and the body, or garment, of a user.

The optional pad 130 may be maintained in place by being attached or coupled to the anti-pinch plate 120. Alternatively, the optional pad 130 may be maintained in relative position by the frictional interaction of apertures that allow the band 140 to pass through the pad 130.

Figure 4A:
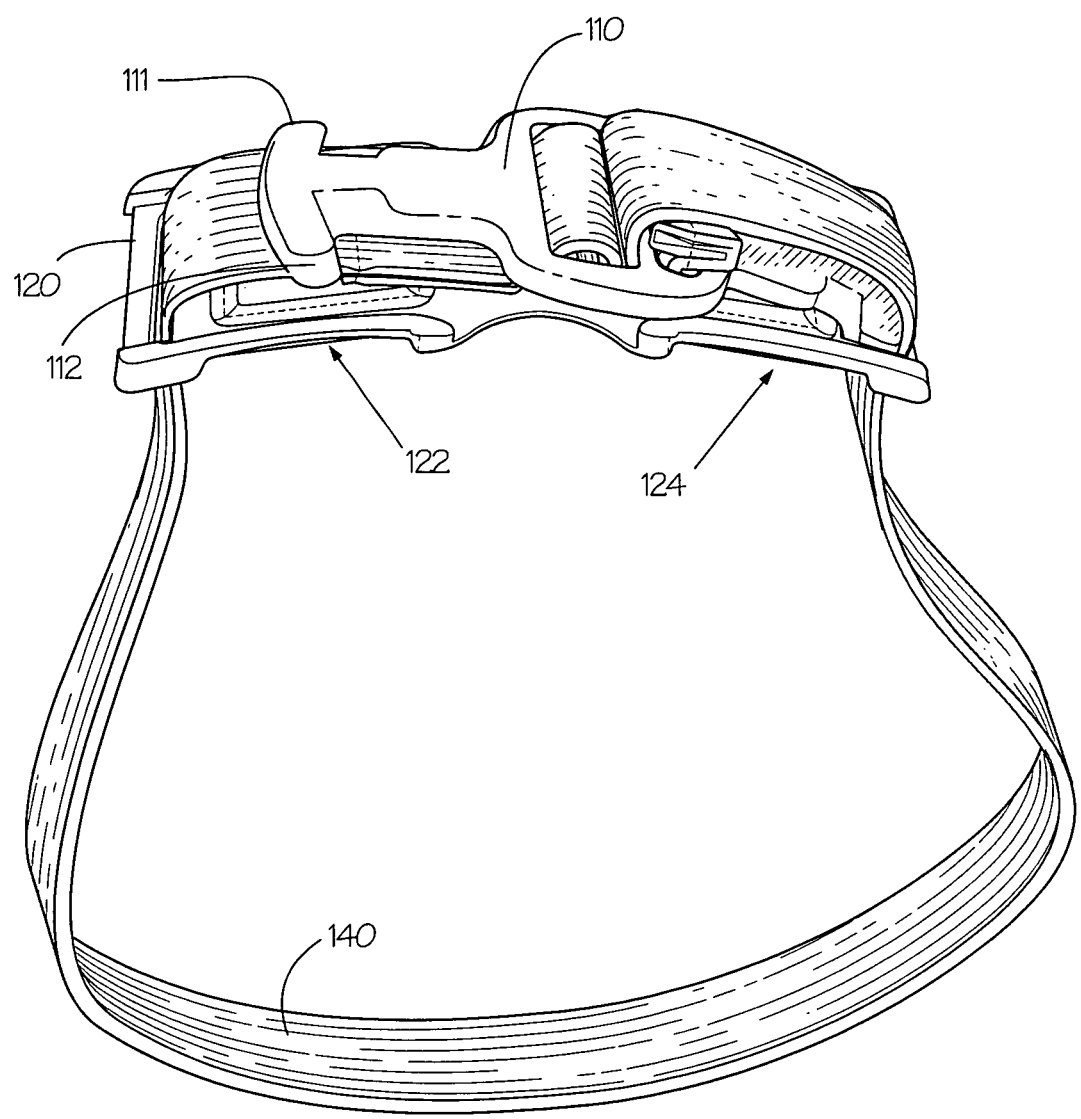
FIG. 4A shows a perspective view of a first exemplary embodiment of a tourniquet system according to this invention, wherein an initial step in the application of the tourniquet system is illustrated.
Figure 4B:
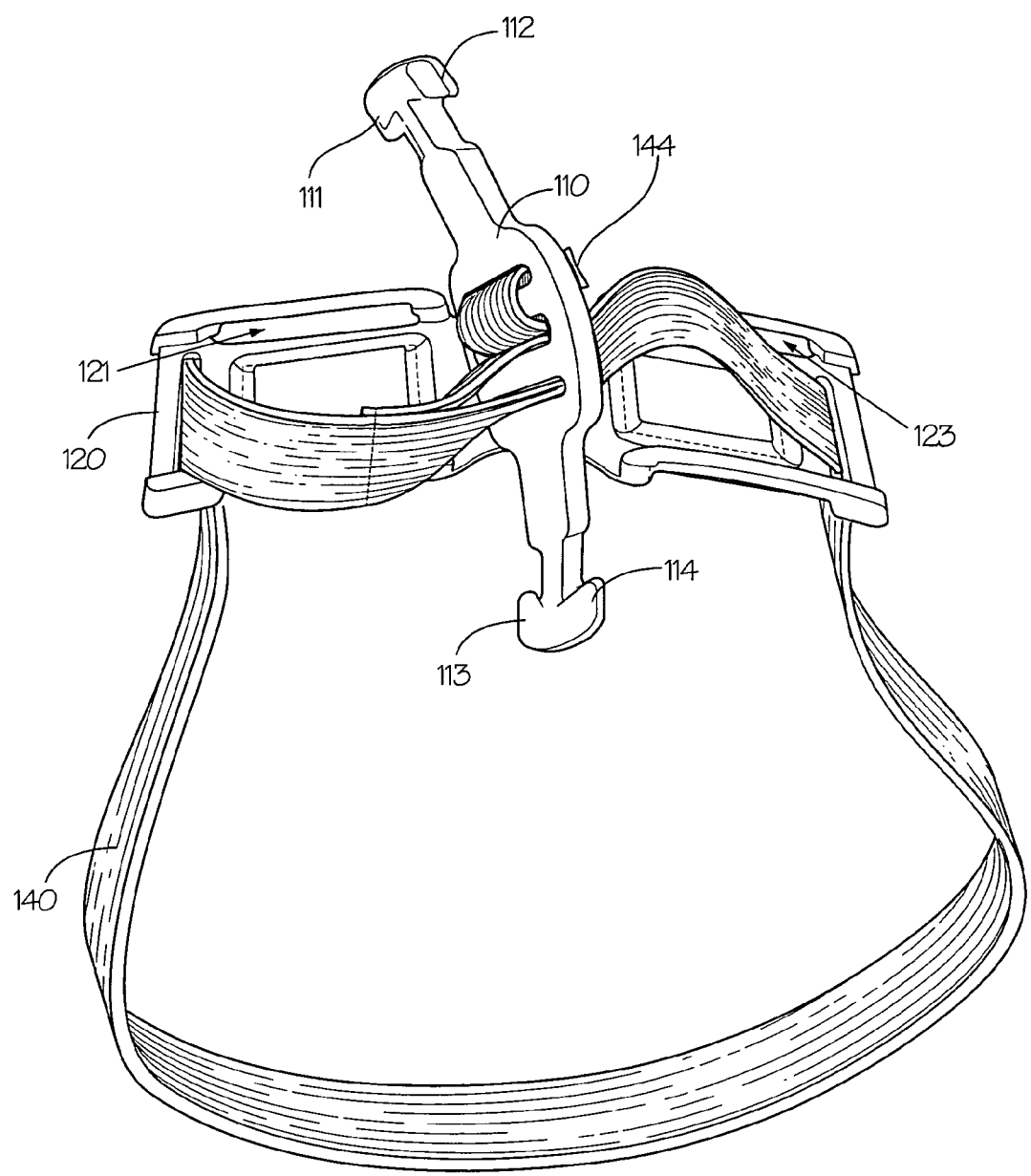
FIG. 4B shows a perspective view of a first exemplary embodiment of a tourniquet system according to this invention, wherein a subsequent step in the application of the tourniquet system is illustrated.
Figure 4C:
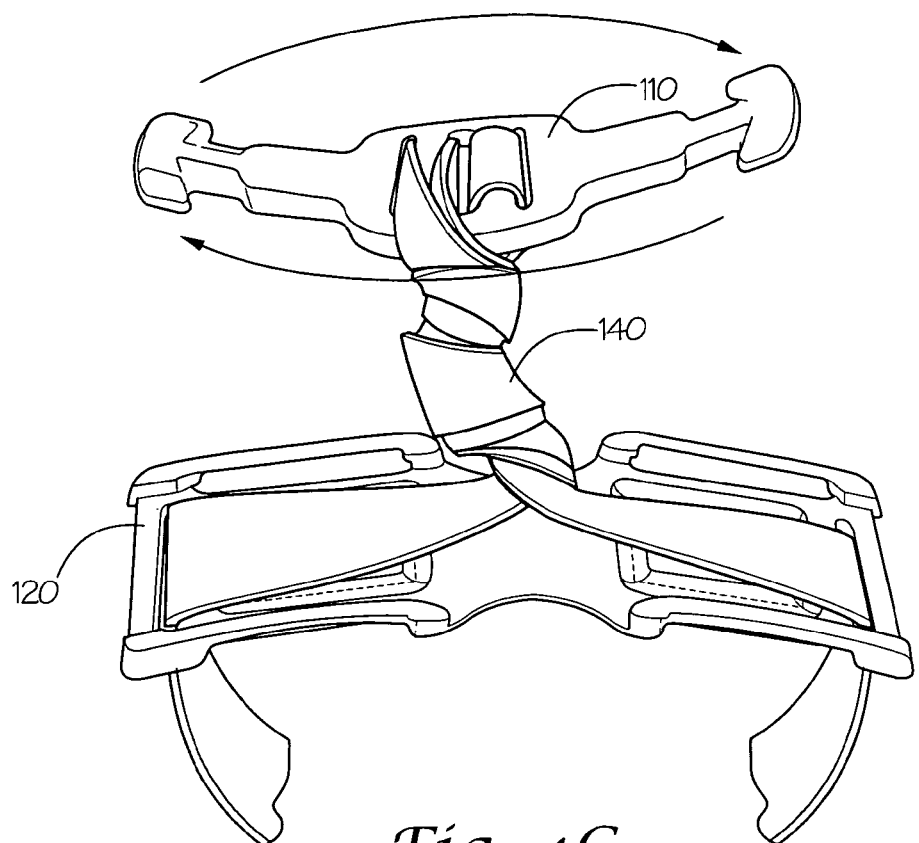
FIG. 4C shows a perspective view of a first exemplary embodiment of a tourniquet system according to this invention, wherein a successive step in the application of the tourniquet system is illustrated.

FIGS. 4A-4E illustrate the application of the exemplary tourniquet system 100. As illustrated in FIGS. 4A-4C, when in use, the tourniquet system 100 is initially placed around an extremity (not shown) and the bar 110 is released from the anti-pinch plate 120 and repositioned such that the band 140 is between the bar 110 and the anti-pinch plate 120. In various exemplary embodiments wherein the curvature of the bar 110 substantially follows the curvature of the anti-pinch plate 120, the bar 110 is repositioned such that the curvature of the bar 110 is opposite the curvature of the anti-pinch plate 120.

Once the bar 110 is repositioned, the bar 110 is twisted or turned, as illustrated in FIG. 4C. As the bar 110 is twisted or turned, the slack of the band 140 is taken up and the band 140 is tightened around the extremity to create pressure. As the bar 110 continues to be twisted, additional pressure is created by the band 140.

Figure 4D:
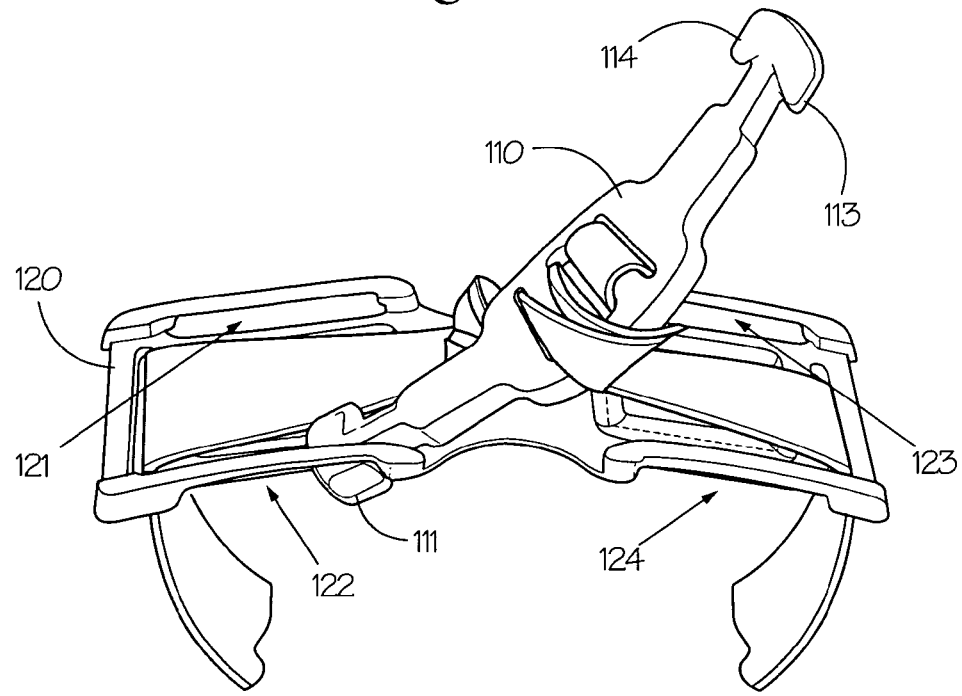
FIG. 4D shows a perspective view of a first exemplary embodiment of a tourniquet system according to this invention, wherein a first possible final step in the application of the tourniquet system is illustrated.
Figure 4E:
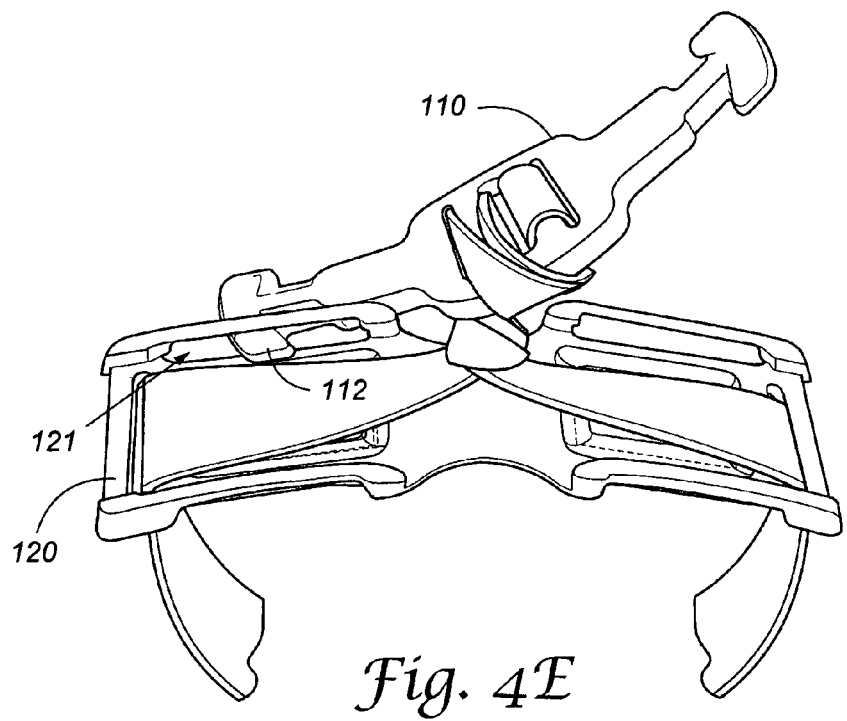
FIG. 4E shows a perspective view of a first exemplary embodiment of a tourniquet system according to this invention, wherein a second possible final step in the application of the tourniquet system is illustrated.

As illustrated in FIG. 4D or FIG. 4E, when an appropriate amount of pressure to the extremity is reached, a bar locking indention or "T" extension 111, 112, 113, or 114 may be held in position by a locking notch 121, 122, 123, or 124 of the anti-pinch plate 120.

If it is desired that the pressure be released, the bar locking indention or "T" extension 111, 112, 113, or 114 may be unlocked from the locking notch 121, 122, 123, or 124, such that the tourniquet system 100 can be reversed or removed altogether.

In certain exemplary embodiments, if the locking notches 121, 122, 123, or 124 are not included, the bar locking indention or "T" extension may be locked into position along an appropriate edge, notch, hole, aperture, loop, or other element of the anti-pinch plate 120.

If a second end portion 144 of the band 140 is free to be pulled, such that excess slack of the band 140 may be taken up, the free end of the band 140 may be pulled (either before or after the bar 110 is repositioned) so that at least a certain amount of excess slack can be taken up before the bar 110 is twisted to tighten the band 140. In this manner, fewer twists of the bar 110 are necessary for the band 140 to be tightened to create the necessary amount of pressure.

In various exemplary embodiments, the bar 110 includes a hinged bar extension that can be extended at one end of the bar 110 to provide additional leverage when utilizing the tourniquet system.

Figure 5:
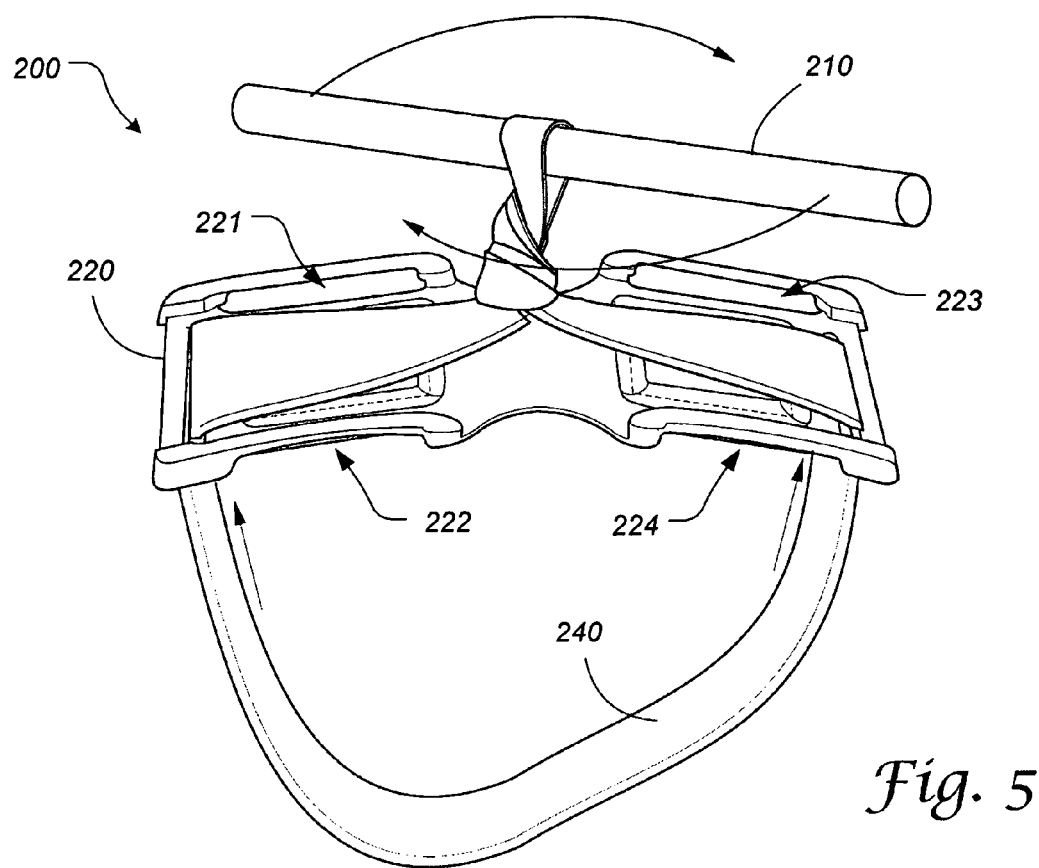
FIG. 5 shows a perspective view of a second exemplary embodiment of a tourniquet system according to this invention.

FIG. 5 shows a perspective view of a second exemplary embodiment of a tourniquet system according to this invention. As illustrated in FIG. 5, the tourniquet system 200 includes an anti-pinch plate 220 and a band 240.

It should be understood that each of these elements corresponds to and operates similarly to the anti-pinch plate 120 and the band 140, as described above with reference to the tourniquet system 100.

However, as shown in FIG. 5, the band 240 comprises a band that has been joined to form a continuous band 240. Additionally, the integral bar 110 is replaced with a separate, attached, or unattached, bar 210.

During use of the tourniquet system 200, the tourniquet system 200 is initially placed around an extremity and the bar 210 is positioned between the band 240 and the anti-pinch plate 220.

Once the bar 210 is positioned, the bar 210 is twisted or turned such that the slack of the band 240 is taken up and the band 240 is tightened around the extremity to create pressure. As the bar 210 continues to be twisted, additional pressure is created by the band 240.

When an appropriate amount of pressure to the extremity is reached, the bar 210 may be held in position by a locking notch 221, 222, 223, or 224 or an appropriate edge, notch, hole, aperture, loop, or other element of the anti-pinch plate 220. It should be appreciated that if a simple bar, such as the locking bar 210, is to be used, the shape of the locking notches 221, 222, 223, or 224 may be altered to allow the locking notches 221, 222, 223, or 224 to be capable of holding the bar in position. For example, one or more of the locking notches 221, 222, 223, or 224 may form a hook, protrusion, indention, notch, or other overall shape capable of holding the bar in position.

If it is desired that the pressure be released, the bar 210 may be unlocked from the locking notch 221, 222, 223, or 224, such that the tourniquet system 200 can be reversed or removed altogether.

Figure 6:
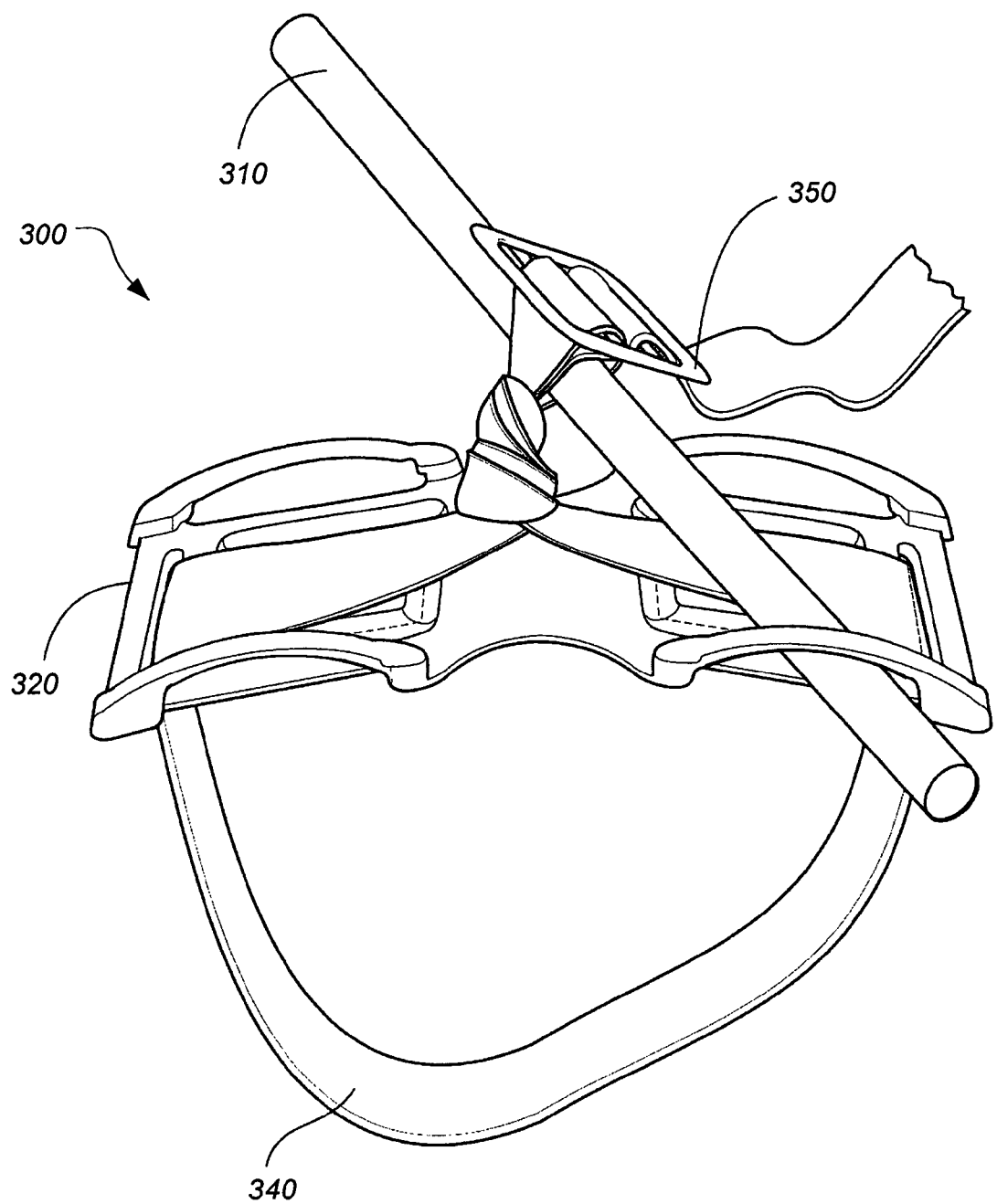
FIG. 6 shows a perspective view of a third exemplary embodiment of a tourniquet system according to this invention.

FIG. 6 shows a perspective view of a third exemplary embodiment of a tourniquet system according to this invention. As illustrated in FIG. 6, the tourniquet system 300 includes a bar 310, an anti-pinch plate 320, and a band 340.

It should be understood that the bar 310 and the anti-pinch plate 320 correspond to and operates similarly to the bar 210 and the anti-pinch plate 220, as described above with reference to the tourniquet system 200.

However, as shown in FIG. 6, the band 340 comprises a band that has a first end that is joined to a buckle 350 and a second end that merely looped through the buckle 350 so that it is free to be pulled so that excess slack of the band 340 may be taken up.

Thus, during use of the tourniquet system 300, the free end of the band 340 may initially be pulled so that at least a certain amount of excess slack in the band 340 can be taken up before the bar 310 is twisted (as described above, with reference to FIG. 5) to tighten the band 340. In this manner, fewer twists of the bar 310 are necessary for the band 340 to be tightened to create the necessary amount of pressure.

Figure 7:
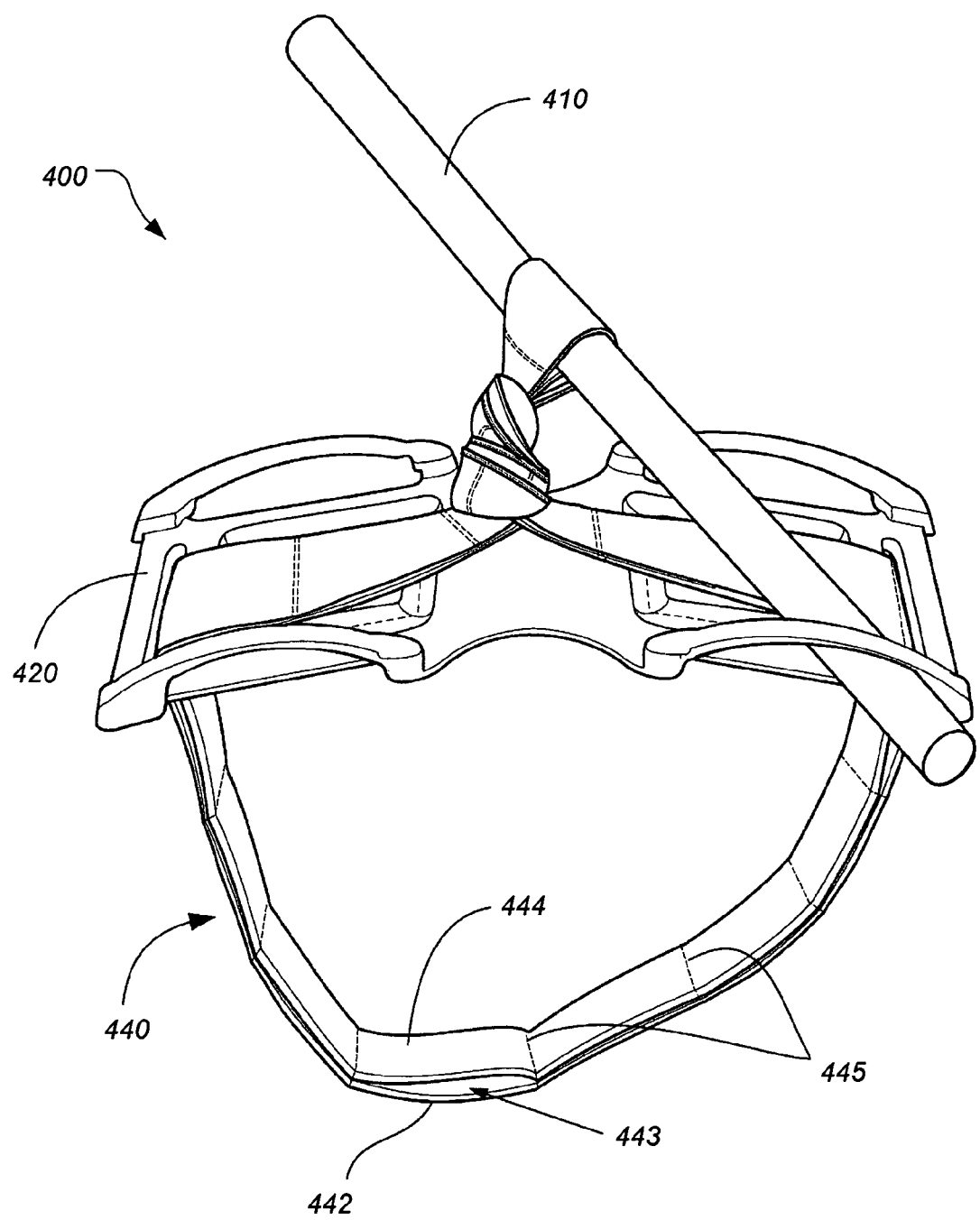
FIG. 7 shows a perspective view of a fourth exemplary embodiment of a tourniquet system according to this invention.

FIG. 7 shows a perspective view of a fourth exemplary embodiment of a tourniquet system according to this invention. As illustrated in FIG. 7, the tourniquet system 400 includes a bar 410, an anti-pinch plate 420, and a band 440.

It should be understood that the bar 410 and the anti-pinch plate 420 correspond to and operates similarly to the bar 210 and/or 310 and the anti-pinch plate 220 and/or 320, as described above with reference to the tourniquet systems 200 and/or 300.

However, as shown in FIG. 7, the band 440 comprises a first, or primary, band 442 and a second, or secondary band 444. The primary and secondary bands are secured to each other at spaced apart locations 445, such that a tunnel segment 443 is formed between the primary band 442 and the secondary band 444 between each secured location 445. Each of the tunnel segments is formed substantially perpendicular to a longitudinal direction of the band 440.

Thus, during use of the tourniquet system 400, the bar 410 may be placed within a tunnel segment of the band 440 before the bar 410 is twisted (as described above) to tighten the band 440.

It should also be understood that the band 410 may either be formed of a joined, continuous band (as discussed above, with respect to tourniquet system 200) or a band having a first end that is joined to a buckle 350 and a second end that merely looped through the buckle 350 so that it is free to be pulled (as discussed above, with respect to tourniquet system 300).

Figure 8A:
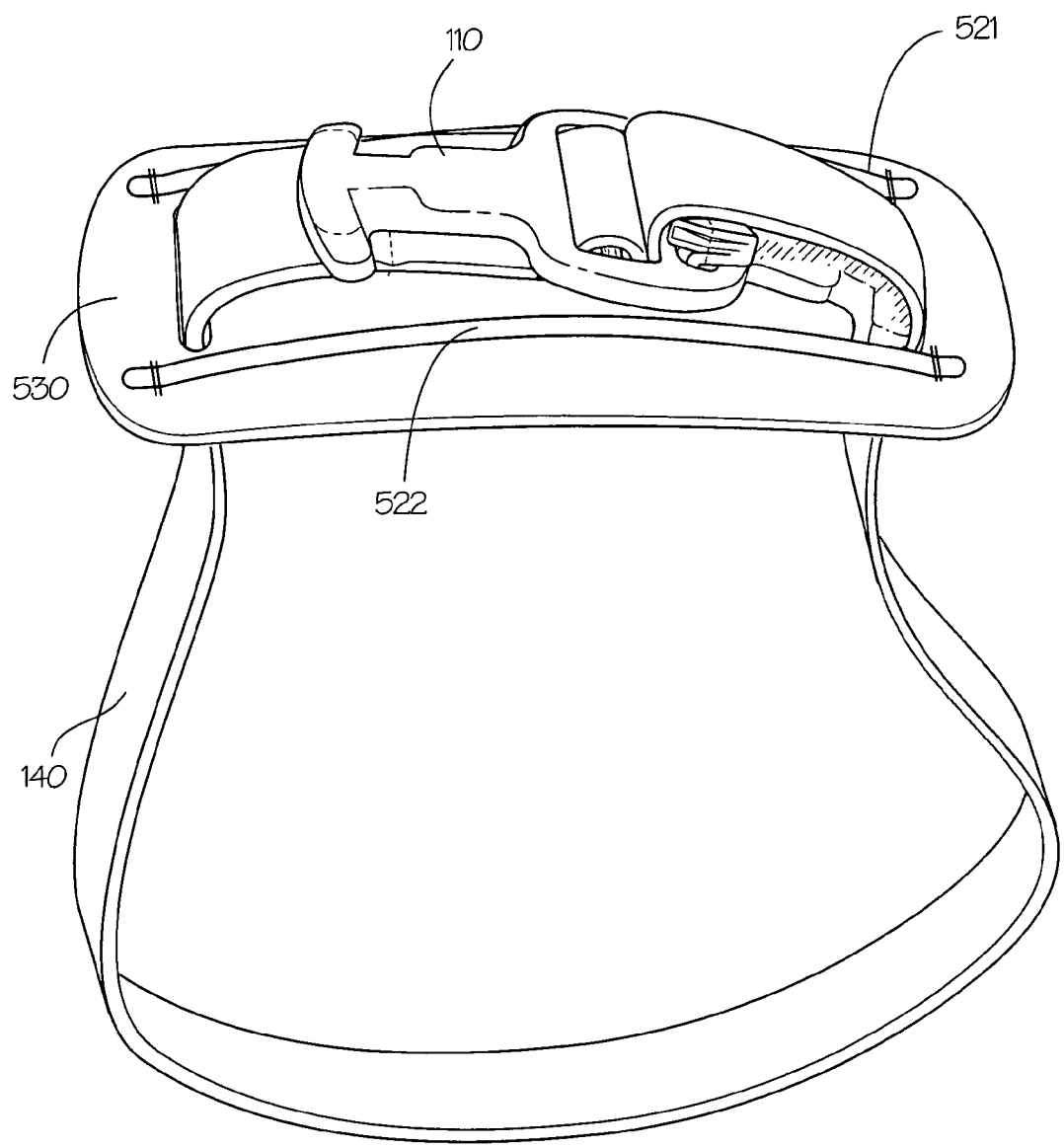
FIG. 8A shows a perspective view of a fifth exemplary embodiment of a tourniquet system according to this invention, wherein an initial step in the application of the tourniquet system is illustrated.
Figure 8B:
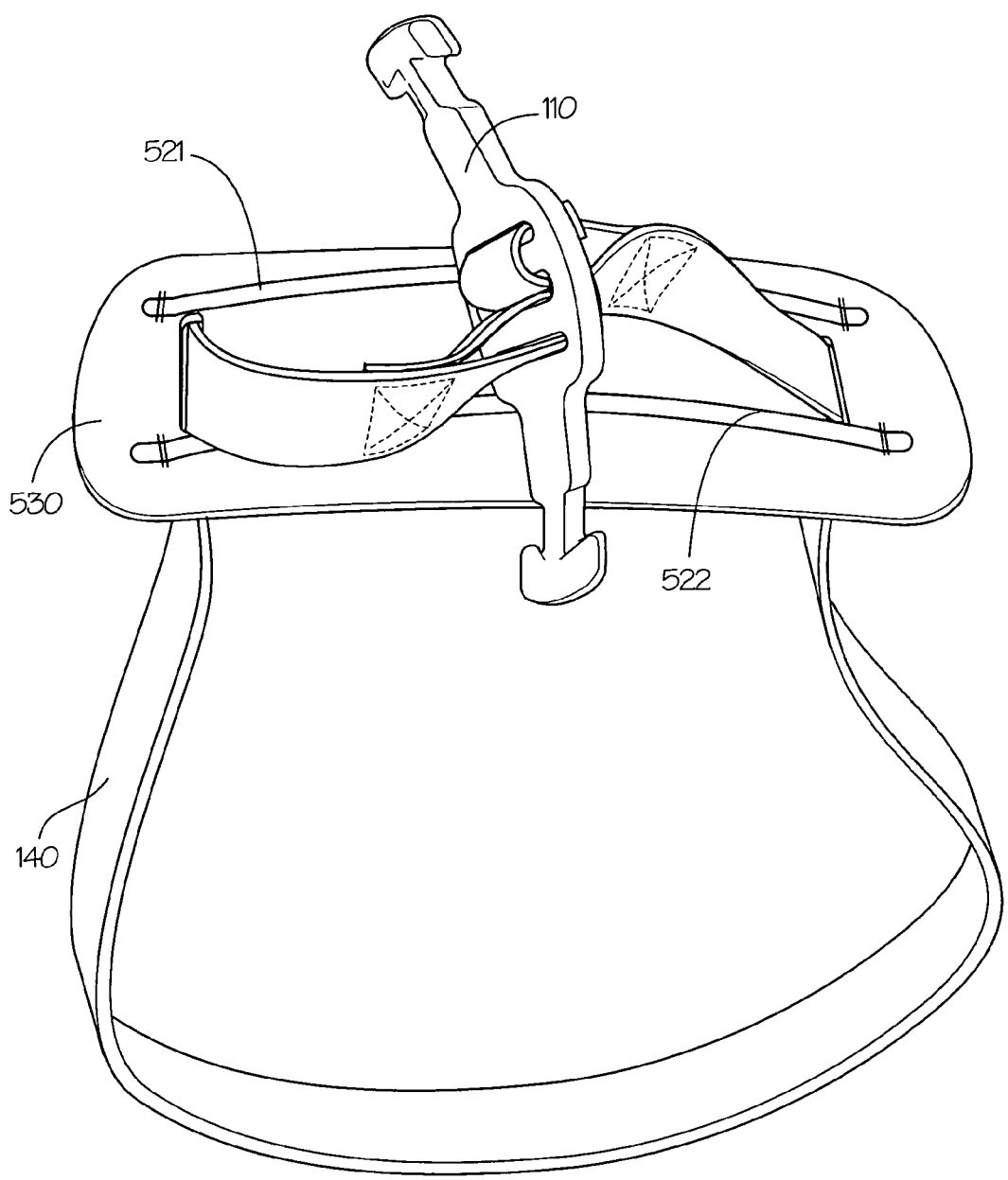
FIG. 8B shows a perspective view of the fifth exemplary embodiment of a tourniquet system according to this invention, wherein a subsequent step in the application of the tourniquet system is illustrated.
Figure 8C:
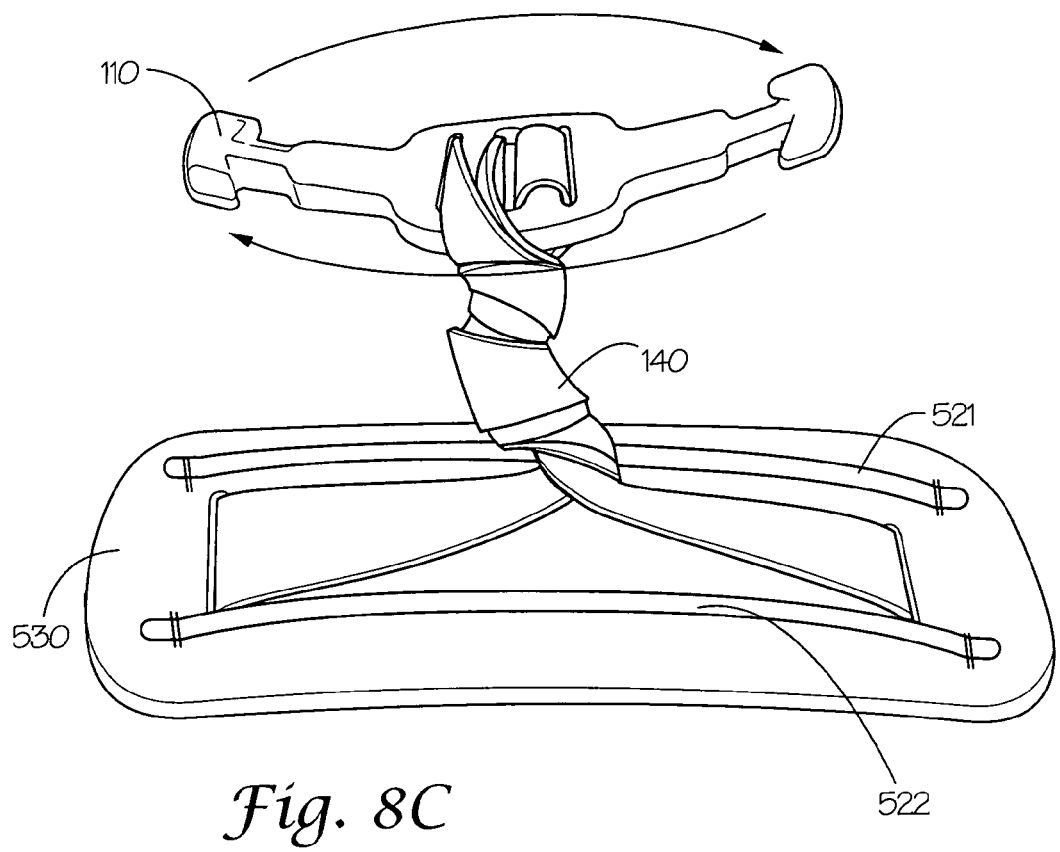
FIG. 8C shows a perspective view of the fifth exemplary embodiment of a tourniquet system according to this invention, wherein a successive step in the application of the tourniquet system is illustrated.

FIGS. 8A-8D illustrate the application of a fifth exemplary embodiment of a tourniquet system according to this invention. As illustrated in FIGS. 8A-8C, the fifth exemplary embodiment of the tourniquet system includes at least some of a bar 110, an anti-pinch plate 530, and a band 140.

It should be understood that the bar 110 and the band 140 correspond to and operate similarly to the bar 110 and the band 140, as described above with reference to the tourniquet system 100. Alternatively, the bar 100 and the band 140 may correspond to or operate similarly to the bar 210, 310, or 410 and/or the band 240, 340, or 440, as described above, with reference to tourniquet systems 200, 300, and/or 400.

However, as shown in FIGS. 8A-8C, the anti-pinch plates 120, 220, 320, and 420 (as illustrated in reference to tourniquet systems 100, 200, 300, and/or 400, respectively) are replaced with an anti-pinch plate 530. Furthermore, the function of the locking notches 121, 122, 123, or 124 of the anti-pinch plate 120 (or the similar locking notches of the anti-pinch plates 220, 320, and/or 420) is essentially replaced by stabilizing cords 521 and 522.

In various exemplary embodiments, the anti-pinch plate 530 may comprise a fabric, natural material, synthetic material, rubber, rubberized, or other flexible material, such as, for example, neoprene. The anti-pinch plate 530 provides a level of cushioning between the bar 110, the band 140, and the body, or garment, of a user.

The anti-pinch plate 530 may be maintained in relative position by the frictional interaction of apertures that allow the band 140 to pass through the anti-pinch plate 530.

The stabilizing cords 521 and 522 are secured to, through, or proximate the anti-pinch plate 530. The stabilizing cords 521 and 522 may be secured at one or more points and provide a means for trapping or securing the bar 110, as described and shown herein. The stabilizing cords 521 and 522 may comprise, for example, 550 cord, or any other substantially elastic or nonelastic cord or banding material. It should be appreciated that the stabilizing cords 521 and 522 may also include any appropriate notch, hole, aperture, loop, or other element capable of securing, trapping, or holding a portion of the bar 110.

In various exemplary embodiments, the "T" shaped extension(s) 111, 112, 113, and/or 114 of the bar 110 are formed so as to allow the bar 110 to be releasably secured to the anti-pinch plate 530, via the interaction of the "T" shaped extension(s) and the stabilizing cords 521 and 522, when the tourniquet system is not in use. Alternatively, the anti-pinch plate 530 may comprise an additional component formed so as to allow the bar 110 to be releasably secured to or within the anti-pinch plate 530, when the tourniquet system is not in use.

As further illustrated in FIGS. 8A-8C, when in use, the band 140 of the tourniquet system is initially placed around an extremity (not shown) and the bar 110 is released from the anti-pinch plate 530 and repositioned such that the band 140 is between the bar 110 and the anti-pinch plate 530. In various exemplary embodiments wherein the curvature of the bar 110 substantially follows the curvature of the anti-pinch plate 530, the bar 110 is repositioned such that the curvature of the bar 110 is opposite the curvature of the anti-pinch plate 530.

Once the bar 110 is repositioned, the bar 110 is twisted or turned, as illustrated in FIG. 8C. As the bar 110 is twisted or turned, the slack of the band 140 is taken up and the band 140 is tightened around the extremity to create pressure. As the bar 110 continues to be twisted, additional pressure is created by the band 140.

Figure 8D:
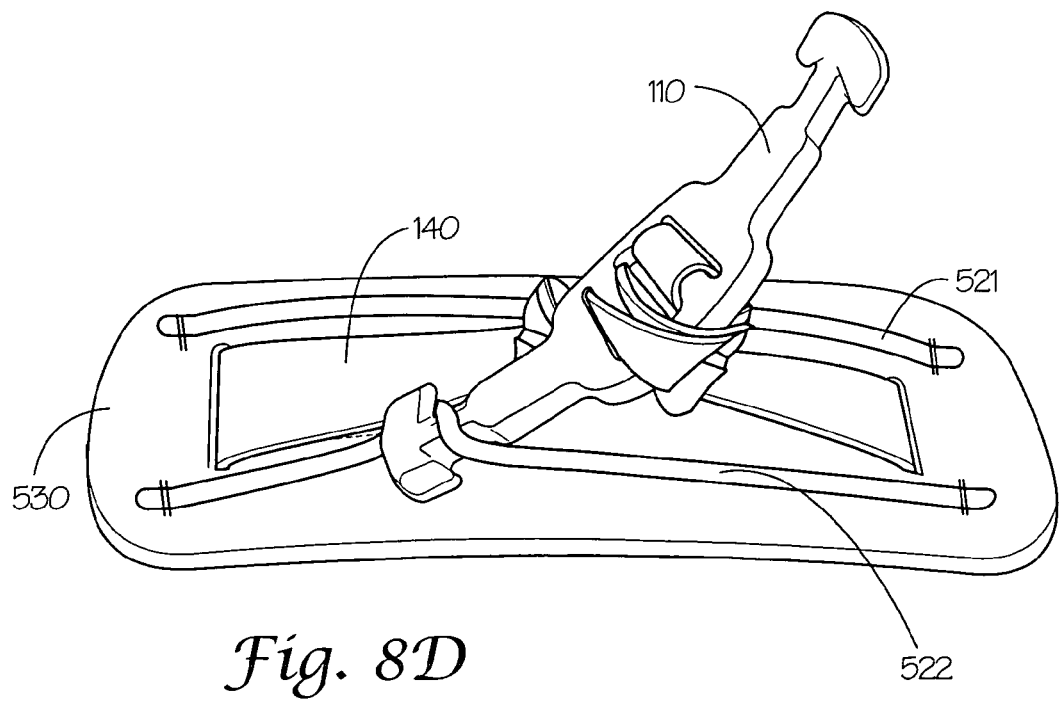
FIG. 8D shows a perspective view of the fifth exemplary embodiment of a tourniquet system according to this invention, wherein a first possible final step in the application of the tourniquet system is illustrated.

As illustrated in FIG. 8D, when an appropriate amount of pressure to the extremity is reached, a bar locking indention or "T" extension 111, 112, 113, or 114 of the bar 110 may be held in position by interaction with at least one of the stabilizing cords 521 and 522 of the anti-pinch plate 530.

If it is desired that the pressure be released, the bar locking indention or "T" extension 111, 112, 113, or 114 may be unlocked from the stabilizing cord 521 and/or 522, such that the tourniquet system can be reversed or removed altogether.

Figure 9:
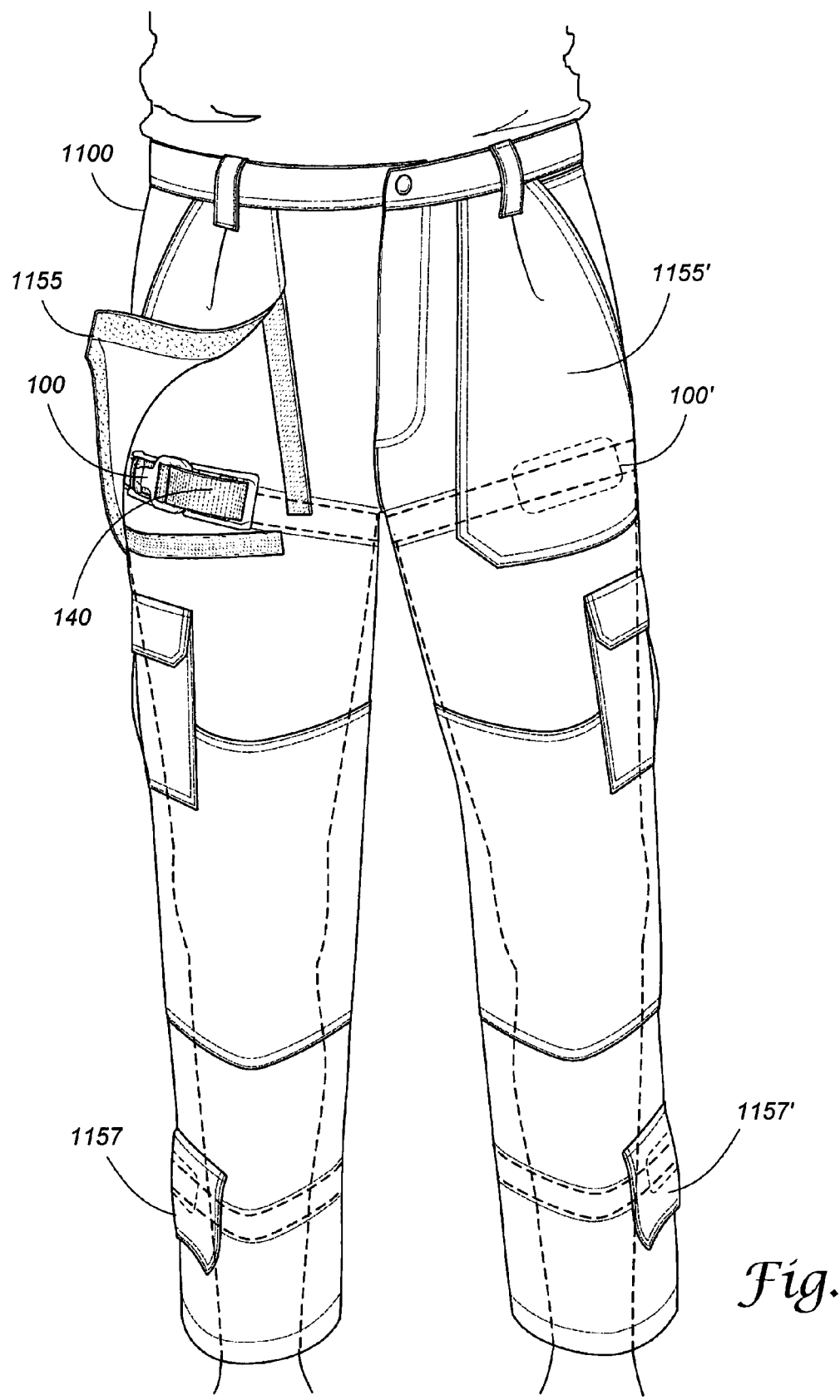
FIG. 9 shows a front view of an exemplary embodiment of a tourniquet system incorporated into a pair of pants, according to this invention.

FIG. 9 shows a front view of an exemplary embodiment of a tourniquet system 100 incorporated into a pair of pants 1100, according to this invention. It should be appreciated that the pants 1100 are merely for exemplary purposes and the pants 1100 could be of other types. It should be appreciated that while the illustrated tourniquet system is designated tourniquet system 100, the tourniquet system 100 as incorporated into the pants 1100 may utilize any of the features described herein with respect to any exemplary embodiment of a stand-alone tourniquet or tourniquet system according to this invention.

As illustrated in FIG. 9, the pants 1100 optionally include four embedded internal tourniquet systems, each having an associated access aperture formed in the pants 1100. In various exemplary, nonlimiting embodiments, the access aperture is covered or concealed by a flap 1155, 1155', 1157, or 1157' that acts to protect the tourniquet system during times of non-use and maintain a smooth appearance to the pants 1100, while allowing quick access when tourniquet use is required.

Figure 12:
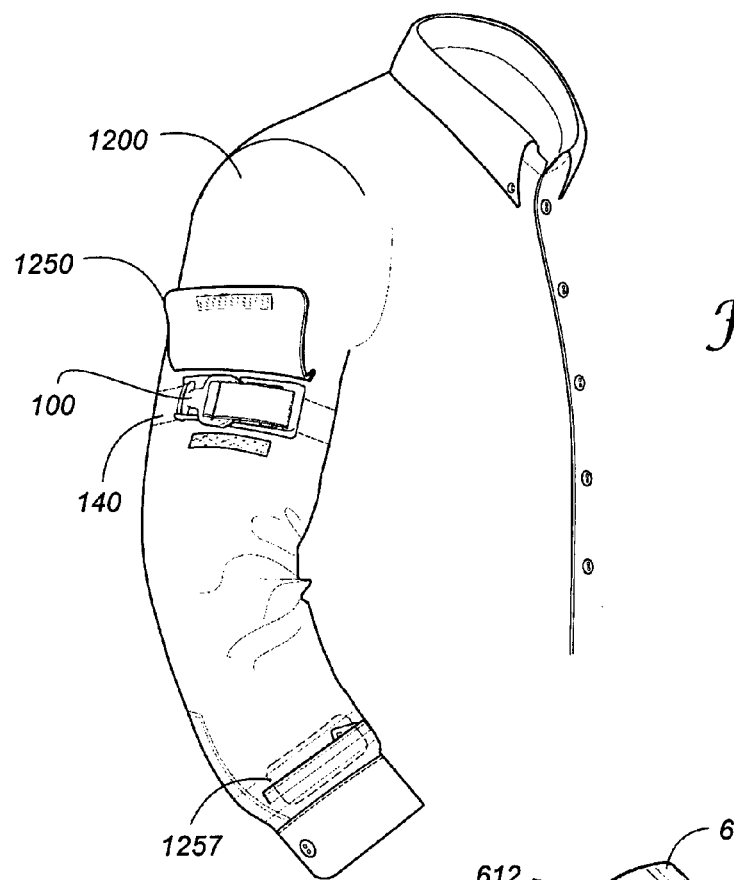
FIG. 12 illustrates an exemplary embodiment of a tourniquet system incorporated into a shirt, according to this invention.

It should be appreciated that the number and placement of embedded internal tourniquet systems and flaps is a design choice based upon the desired appearance and/or functionality of the pants 1100. It should also be understood that the flaps may represent any type of sealable and/or resealable access aperture, such as, for example, the zippered access aperture 1257, as illustrated in FIG. 12. In various exemplary embodiments, each of the flaps is releasably secured to the pants 1100 by, for example, hook and loop fasters or other suitable quick release connectors.

In various exemplary, nonlimiting embodiments, flaps 1155 and 1155' are located such that the tourniquet bands 140 of the internal tourniquet systems 100 and 100' are located proximate an upper portion of the leg portion of the pants 1100 and flaps 1157 and 1157' are located such that the tourniquet bands 140 of the internal tourniquet systems associated with flaps 1157 and 1157' are located proximate a lower portion of the leg portion of the pants 1100.

In various other exemplary, nonlimiting embodiments, flaps 1155 and 1155' are located such that the tourniquet bands 140 of the internal tourniquet systems 100 and 100' are centered proximate the inguinal crease and flaps 1157 and 1157' are located such that the tourniquet bands 140 of the internal tourniquet systems associated with flaps 1157 and 1157' are centered proximate the tibial tuberosity.

In still other exemplary, nonlimiting embodiments, flaps 1155 and 1155' are located such that the tourniquet bands 140 of the internal tourniquet systems 100 and 100' are centered approximately two centimeters distal to the inguinal crease and flaps 1157 and 1157' are located such that the tourniquet bands 140 of the internal tourniquet systems associated with flaps 1157 and 1157' are centered approximately two centimeters distal to the tibial tuberosity.

In various exemplary, nonlimiting embodiments, flaps 1155 and 1155' comprise at least a portion of a main pocket of the pants 1100. Thus, to access the tourniquet system 100 or 100', a portion of the main pockets of the pants 1100 is released from the main body of the pants 1100 for easy access.

As illustrated in FIG. 9, the tourniquet system band 140 is positioned or attached within a channel or tunnel formed in the pants 1100. In this manner, at least a portion of the band 140 is secured proximate an inner surface of the pants 1100 such that the tourniquet system is maintained in a desired location relative to the pants 1100 and/or the body of the user. Additionally, the fabric of the pants 1100 may be a means of protecting the integrity of the band 140 positioning the band 140 within the garment.

The band 140 may be secured within the pants 1100 in any suitable manner that may include sewing, adhering, or molding such that a channel, tunnel, or series of loops is formed that is slightly larger than the band 140. The formed channel or tunnel may be formed around the entire circumference of the inner surface of the pants 1100 or may be formed around only a portion of the circumference of the inner surface of the pants 1100.

In various exemplary embodiments, the band 140 is located within the channel or tunnel in such a manner that the surface of the band 140 is adjacent, but not noticeably impeded by, the interaction of the surface of the band 140 and the pants 1100 such that when the tourniquet is tightened or loosened, the band 140 is relatively free to move within the channel or tunnel.

In various exemplary embodiments, the anti-pinch plate 120 (or the anti-pinch plate 220, 320, 420, or the anti-pinch plate 530) may be attached or coupled to an exterior or interior portion of the pants 1100. The anti-pinch plate may be attached or coupled such that the entire anti-pinch plate is attached or coupled to the pants 1100. Alternatively, select portions of the anti-pinch plate may be attached or couple the pants 1100.

Figure 10:
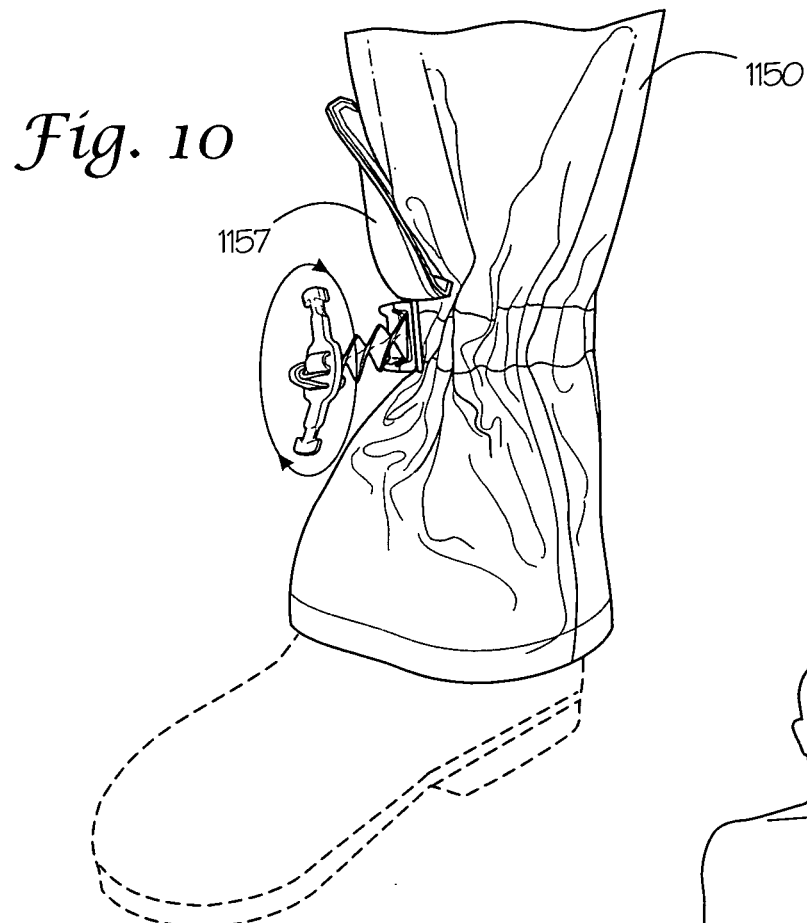
FIG. 10 illustrates an exemplary embodiment of a tourniquet system incorporated into a pair of pants, according to this invention.

As illustrated in FIG. 10, during use of an exemplary embodiment of a tourniquet system incorporated into a lower portion 1150 of a pair of pants 1100, the flap 1157 is separated from the main body of the pants 1100 and lifted to allow access to the tourniquet system 100. Once access to the tourniquet system 100 is obtained, the tourniquet system 100 may be applied and/or released as described herein.

FIG. 12 shows the tourniquet system 100 positioned or attached within a channel or tunnel formed in a shirt 1200, according to this invention. As illustrated in FIG. 12, the shirt 1200 comprises a full-sleeved, button-down shirt 1200. It should be appreciated that the shirt 1200 is merely for exemplary purposes and the shirt 1200 could be of other types. For example, a shirt 1200 may comprise a short sleeve shirt that only includes upper flap 1250 and a single embedded tourniquet system in each arm portion of the short sleeve shirt.

As illustrated in FIG. 12, flap 1250 is located such that the tourniquet band 140 of the tourniquet system 100 is positioned proximate an upper portion of the arm portion of the shirt 1200 and zippered access aperture 1257 is located such that the tourniquet bands 140 of the internal tourniquet system associated with zippered access aperture 1257 is located proximate a lower portion of the arm portion of the shirt 1200.

In various other exemplary, nonlimiting embodiments, flap 1250 is located such that the tourniquet bands 140 of the internal tourniquet systems 100 is centered proximate a level of superior position of the bicep and zippered access aperture 1257 is located such that the tourniquet bands 140 of the internal tourniquet systems associated with zippered access aperture 1257 is centered proximate the position of the forearm.

In still other exemplary, nonlimiting embodiments, flap 1250 is located such that the tourniquet bands 140 of the internal tourniquet systems 100 and 100' are centered approximately two centimeters from a center of the bicep and zippered access aperture 1257 is located such that the tourniquet bands 140 of the internal tourniquet systems associated with zippered access aperture 1257 is centered approximately two centimeters below the elbow of the wearer.

Figure 11:
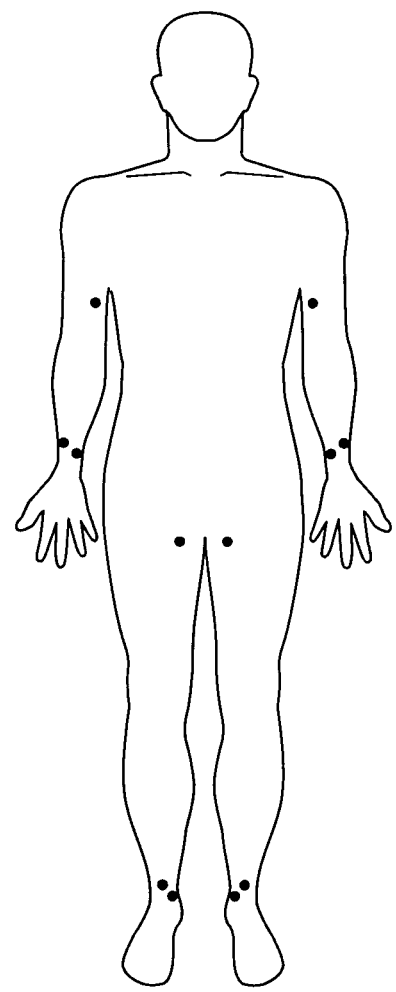
FIG. 11 shows certain exemplary, potential points for applying pressure to the human body to control bleeding

It should be understood that while, in certain exemplary embodiments, the embedded tourniquet systems of the exemplary pants 1100 and shirt 1200 are positioned proximate potential points for applying pressure to the human body to control bleeding, as illustrated in FIG. 11, the number and placement of tourniquet systems is a design choice based upon the desired appearance and/or functionality of the particular garment in which the tourniquet systems are incorporated or embedded.

Figure 13:
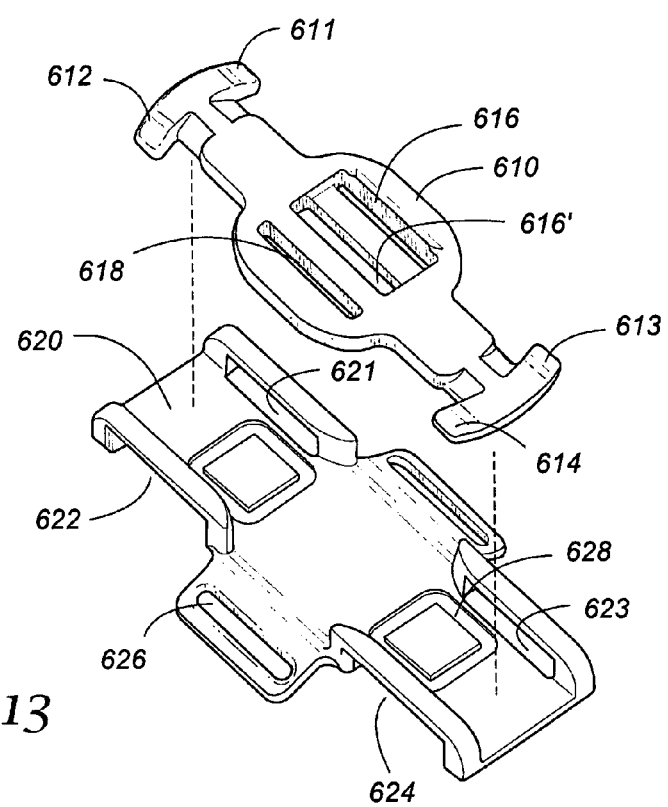
FIG. 13 shows a perspective view of a sixth exemplary embodiment of certain components of a tourniquet system according to this invention.

FIG. 13 shows a perspective view of a sixth exemplary embodiment of certain components of a tourniquet system according to this invention. As illustrated in FIG. 13, the sixth exemplary embodiment of the tourniquet system includes at least some of a bar 610 and an anti-pinch plate 620. The bar 610 comprises substantially "T" shaped extensions 611, 612, 613, and 614 at each of the first end and the second end, respectively, and apertures 616, 616', and 618. The anti-pinch plate 620 comprises locking notch 621, 622, 623, or 624, one or more band receiving apertures 626, and may optionally include a stitchable portion 628.

It should be understood that components of the bar 610 and the anti-pinch plate 620 may correspond to and operate similarly to the bar 110 and the band 140, as described above with reference to the tourniquet system 100. For example, in various exemplary embodiments, the locking notches 621, 622, 623, and/or 624 may comprise a cord or other substantially elastic or non-elastic cord or banding material that is attached or coupled to the anti-pinch plate 620.

Alternatively, the bar 100 and the band 140 may correspond to or operate similarly to the bar 210, 310, 410, or 510 and/or the anti-pinch plate or pad 220, 320, 420, or 530, as described above.

For example, the anti-pinch plate 620 may be supplemented or replaced by an anti-pinch plate, which is similar in function and operation to the anti-pinch plate 530, as described above. In various exemplary embodiments, if an anti-pinch plate is utilized, it may be may be utilized in conjunction with one or more stabilizing cords, as described above with reference to stabilizing cords 521 and 522.

However, as shown in FIG. 13, the anti-pinch plate 620 is formed such that a band (not shown) may be oriented in a manner perpendicular to a longitudinal axis of the anti-pinch plate 620. Additionally, the bar 610 is formed such that a band (not shown) may also be oriented in a manner perpendicular to a longitudinal axis of the bar 610.

In this manner, the sixth exemplary embodiment of the tourniquet system may be utilized in applications where the circumference of the limb around which the band is to be placed is insufficient to accommodate the other exemplary embodiments of the tourniquet system. For example, this embodiment of the tourniquet system may be utilized proximate an area such as a wrist or ankle or the circumference of the limb may be relatively small.

Figure 14:
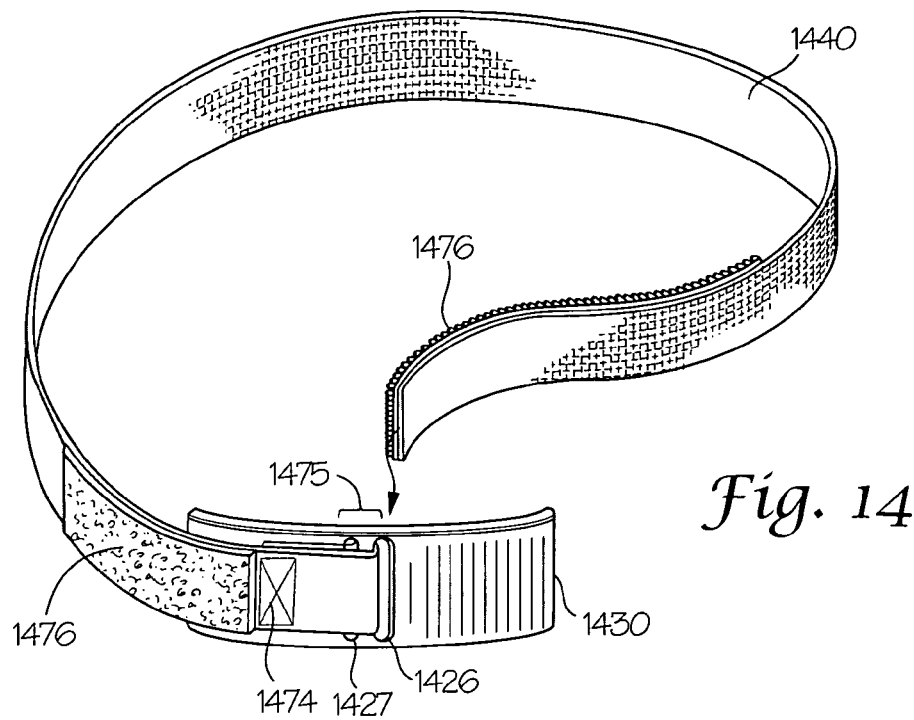
FIG. 14 shows a perspective view of a seventh exemplary embodiment of certain components of a tourniquet system according to this invention.

FIG. 14 shows a perspective view of yet another embodiment of the tourniquet system of the current invention. As illustrated in FIG. 14, the anti-pinch plate 1430 is formed such that the band 1440 is arranged so that a left end portion of the band 1440 is passed through aperture 1426 such that the inner surface of the band 1440 is adjacent to the inner surface of the anti-pinch plate 1430. The left end portion of the band 1440 is then passed through aperture 1427 such that the inner surface of the left end portion of the band 1440 of the band is adjacent to a portion of the inner surface of the band 1440 proximate the left end portion of the band 1440.

Next, the band 1440 is secured to itself in area 1474 in any suitable manner such that a loop 1475 is formed proximate the left end portion of the band 1440 wherein the anti-pinch plate 1430 is secured, via the interaction of the loop 1475 and the apertures 1426 and 1427. The outer surface of the band 1440 adjacent to the point where the tourniquet is secured to itself in area 1474 contains one end of a temporary securing means 1476 (such as a hook and loop fastener). Along the inner surface of the band 1440, proximate the right edge of the band 1440, lies the matching end of the temporary securing means 1476, such that the right edge is passed through the aperture 1426 in a manner that before passing through the right edge of the band 1440 the outer surface of the band 1440 is adjacent to the inner surface of the anti-pinch plate 1430 and after passing through the inner surface of the right edge of the band 1440 overlaps the temporary securing means 1476 such that the temporary securing means 1476 may be used to tighten, secure, release, and/or re-secure the tourniquet system as desired.

Figure 15:
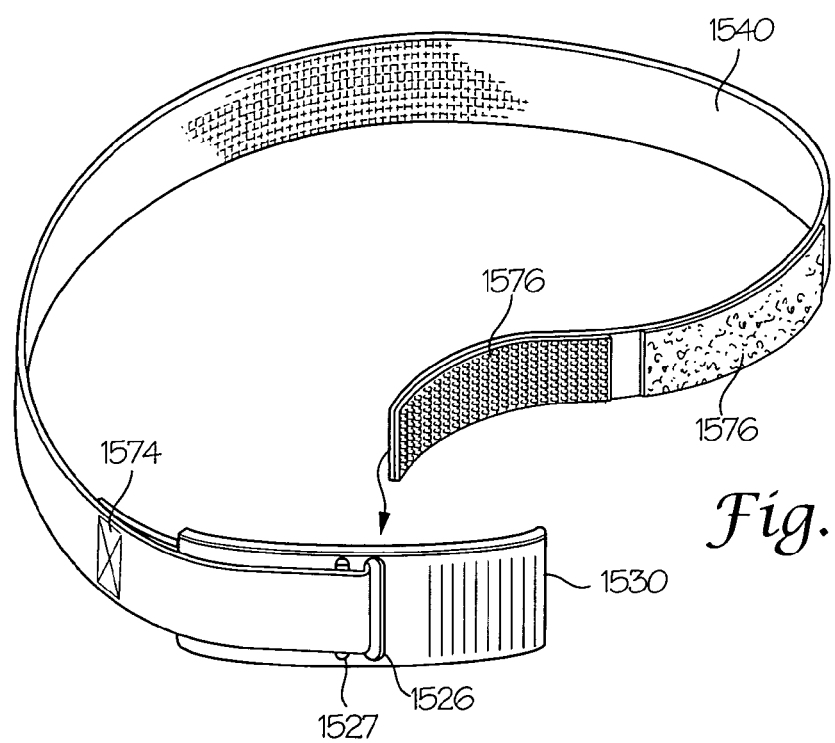
FIG. 15 shows a perspective view of an eighth exemplary embodiment of certain components of a tourniquet system according to this invention.

FIG. 15 shows a perspective view of yet another embodiment of the tourniquet system of the current invention. As illustrated in FIG. 15, the band 1540 is affixed to the anti-pinch plate 1530 such that the inner surface of the left end portion of the band 1540 is passed over the outer surface of the anti-pinch plate 1530. The left end portion of the band 1540 is then passed through aperture 1527 in a manner such that the inner surface of the left end portion of the band 1540 becomes adjacent to the inner surface of the anti-pinch plate 1530 until it meets and overlaps another portion of the inner surface of the band 1540. Somewhere along the area of overlap, the inner surfaces are secured to each other in area 1574 in any suitable manner such that a loop is formed containing approximately half of the anti-pinch plate 1530.

Proximate the outer surface of the right edge of the band 1540 lie two opposing ends of a temporary securing system 1576 (such as A hook and loop fastener). In various exemplary embodiments, the tourniquet system is activated by passing the right edge of the band 1540 through the aperture 1526 such that after passing through aperture 1526 the outer surface of the right edge of the band 1540 is adjacent to the outer surface of the anti-pinch at 1530. The outer surface of the right edge of the band 1540 generally passes beyond the right edge of the anti-pinch plate 1530 and overlaps the outer surface of the band 1540 where the opposing temporary securing means 1576 is located in order to secure the tourniquet when needed.

Figure 16:
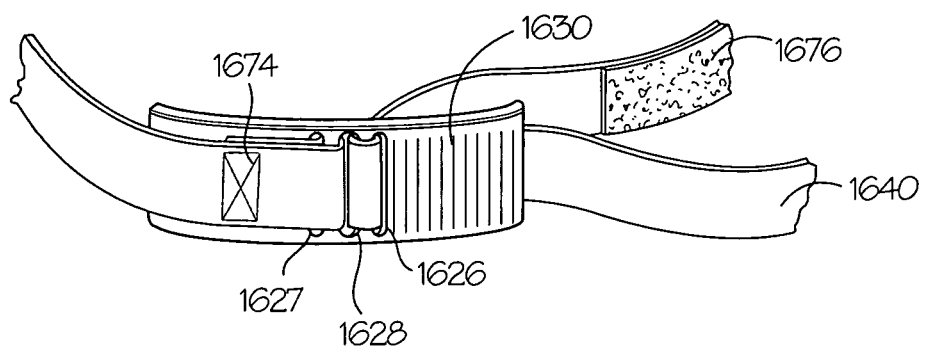
FIG. 16 shows a perspective view of a ninth exemplary embodiment of certain components of a tourniquet system according to this invention.

FIG. 16 shows a perspective view of yet another embodiment of the tourniquet system of the current invention. As illustrated in FIG. 16, the anti-pinch plate 1630 is formed in a similar manner as noted in FIGS. 14 and 15. However, as illustrated in FIG. 16, an additional aperture 1628 is formed between aperture 1627 and aperture 1626.

In various exemplary embodiments, aperture 1628 has a width that is approximately twice the distance between the inner surface and outer surface of the band 1640 and allows two portions of the band 1640 to pass through at the same time with little or no noticeable resistance. As described above with reference to FIG. 14, a loop is again created by passing an end portion of the belt 1640 through aperture 1627 and aperture 1628. Somewhere along the area of overlap, the belt 1640 is secured to itself in area 1674 in any suitable manner.

Unlike the tourniquet system illustrated in FIG. 14, the right edge of the band 1640 is passed through aperture 1628 such that the outer surface of the right edge portion of the band 1640 is adjacent to the outer surface of the anti-pinch plate 1630. The right edge of the band 1640 is then passed through aperture 1626 such that the outer surface of the band 1640 is adjacent to itself and the inner surface of the band 1640 is adjacent to the inner surface of the anti-pinch plate 1630. Placed upon the overlap of the outer surface of the right edge portion of the band 1640, before and after the portion of the band 1640 that is threaded through the aperture 1628 and aperture 1626, are cooperating portions of a temporary securing means 1676, such that the overlapping portion of the band 1640 may be tightened, secured, and released when needed.

Figure 17A:
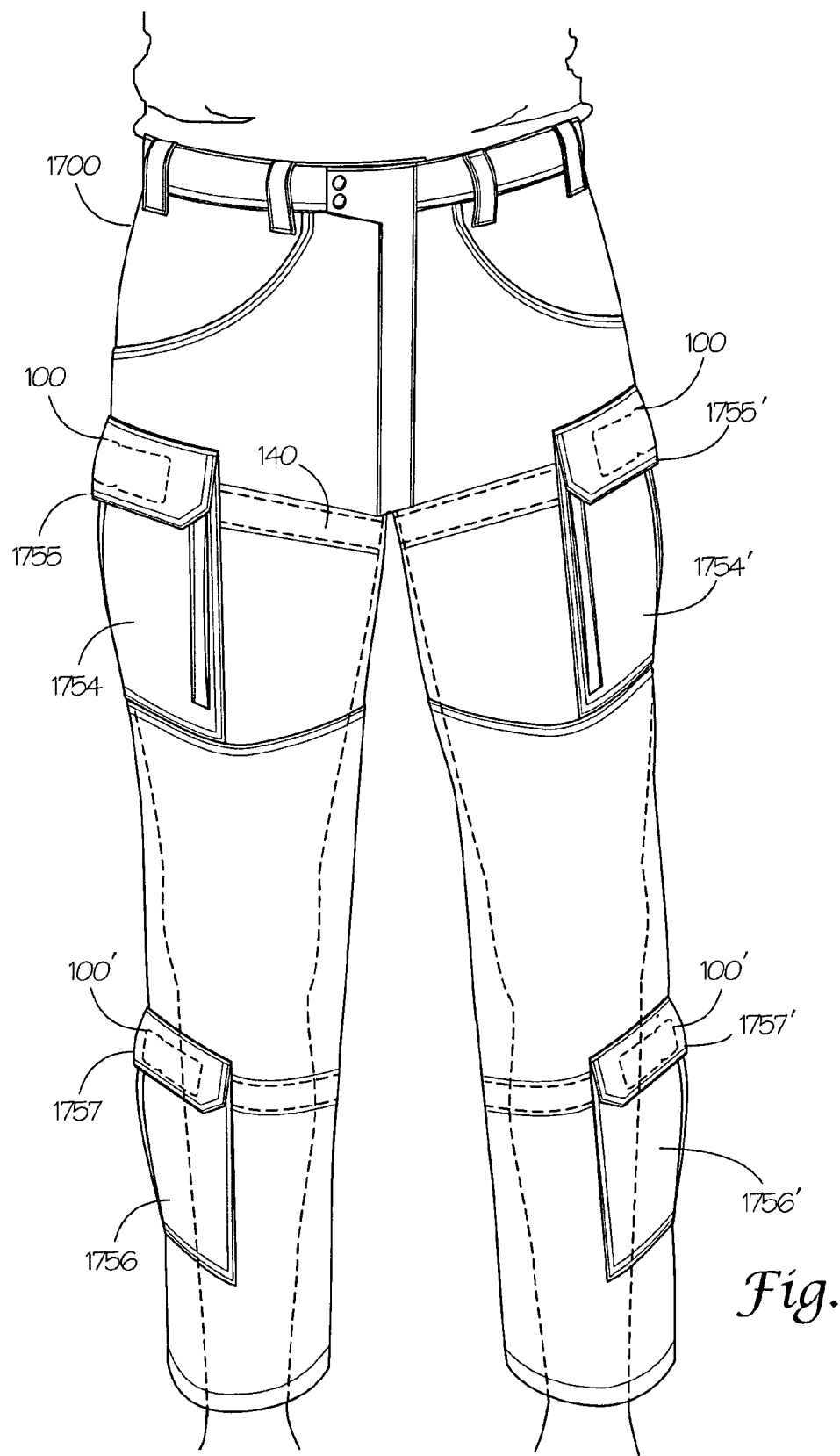
FIG. 17A illustrates an exemplary embodiment of a tourniquet system incorporated into an alternate pair of pants, according to this invention.

FIG. 17A shows a front view of an exemplary embodiment of a tourniquet system 100 incorporated into an alternate pair of pants 1700, according to this invention. It should be appreciated that the pants 1700 are merely for exemplary purposes and the pants 1700 could be of other types. It should also be appreciated that while the illustrated tourniquet systems are designated tourniquet systems 100 and 100', the tourniquet systems 100 and 100' as incorporated into the pants 1700 may utilize any of the features described herein with respect to any exemplary embodiment of a stand-alone tourniquet or tourniquet system according to this invention.

As illustrated in FIG. 17A, the pants 1700 optionally include four embedded internal tourniquet systems, each being accessible via the flap of a cargo-type pocket formed in the pants 1700. In various exemplary, nonlimiting embodiments, the pants 1700 include two cargo pockets 1754 and 1754', each having a flap 1755 and 1755', respectively, for covering access to the interior of the respective cargo pockets 1754 and 1754'. Similarly, the pants 1700 include two, comparatively smaller, cargo pockets 1756 and 1756', each having a flap 1757 and 1757', respectively, for covering access to the interior of the respective cargo pockets 1756 and 1756'. The flaps 1755, 1755', 1757, and 1757' act to protect the tourniquet system during times of non-use and maintain a smooth appearance to the pants 1700, while allowing quick access when tourniquet use is required.

It should be understood that the illustrated tourniquet systems 100 and 100' are similar, however the tourniquet systems 100 are typically of a larger scale than tourniquet systems 100'. In this manner, tourniquet systems 100 are typically positioned around larger limb portions, while the tourniquet systems 100' are typically positioned around smaller limb portions.

It should be appreciated that the number and placement of embedded internal tourniquet systems and flaps is a design choice based upon the desired appearance and/or functionality of the pants 1700. It should also be understood that the flaps may represent any type of sealable and/or resealable access aperture.

Figure 17B:
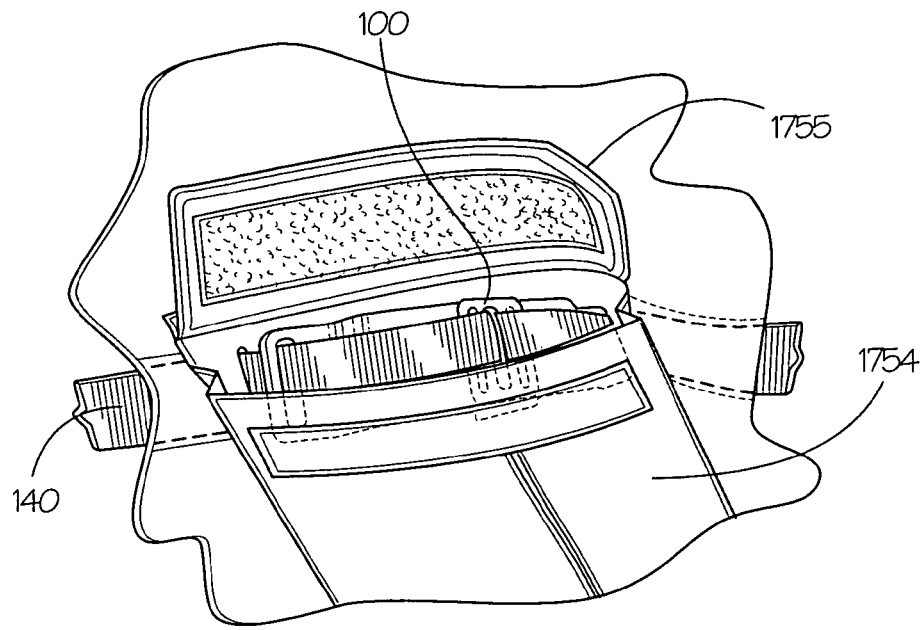
FIG. 17B shows a more detailed view of a tourniquet system incorporated into a first exemplary embodiment of a cargo-type pocket of a pair of pants, according to this invention.

In various exemplary embodiments, as illustrated in FIG. 17B, each of the flaps may be releasably secured to the pants 1700 by, for example, hook and loop fasters or other suitable quick release connectors.

In various exemplary, nonlimiting embodiments, flaps 1755 and 1755' are located such that the tourniquet bands 140 of the internal tourniquet systems 100 are located proximate an upper portion of the leg portion of the pants 1700 and flaps 1757 and 1757' are located such that the tourniquet bands of the internal tourniquet systems 100' associated with flaps 1757 and 1757' are located proximate a lower portion of the leg portion of the pants 1700.

In various other exemplary, nonlimiting embodiments, flaps 1755 and 1755' are located such that the tourniquet bands of the internal tourniquet systems 100 are centered proximate the inguinal crease and flaps 1757 and 1757' are located such that the tourniquet bands of the internal tourniquet systems 100' are centered proximate the tibial tuberosity.

In still other exemplary, nonlimiting embodiments, flaps 1755 and 1755' are located such that the tourniquet bands of the internal tourniquet systems 100 are centered approximately two centimeters distal to the inguinal crease and flaps 1757 and 1757' are located such that the tourniquet bands of the internal tourniquet systems 100' are centered approximately two centimeters distal to the tibial tuberosity.

As illustrated in FIG. 17A, the tourniquet system band 140 is positioned or attached within a channel or tunnel formed in the pants 1700. In this manner, at least a portion of the band 140 is secured proximate an inner surface of the pants 1700 such that the tourniquet system is maintained in a desired location relative to the pants 1700 and/or the body of the user. Additionally, the fabric of the pants 1700 may be a means of protecting the integrity of the band 140 positioning the band 140 within the garment.

The band 140 may be secured within the pants 1700 in any suitable manner that may include sewing, adhering, or molding such that a channel, tunnel, or series of loops is formed that is slightly larger than the band 140. The formed channel or tunnel may be formed around the entire circumference of the inner surface of the pants 1700 or may be formed around only a portion of the circumference of the inner surface of the pants 1700.

In various exemplary embodiments, the band 140 is located within the channel or tunnel in such a manner that the surface of the band 140 is adjacent, but not noticeably impeded by, the interaction of the surface of the band 140 and the pants 1700 such that when the tourniquet is tightened or loosened, the band 140 is relatively free to move within the channel or tunnel.

In various exemplary embodiments, the anti-pinch plate of the internal tourniquet system 100 and/or 100' may be attached or coupled to an exterior or interior portion of the pants 1700. The anti-pinch plate may be attached or coupled such that the entire anti-pinch plate is attached or coupled to the pants 1700. Alternatively, select portions of the anti-pinch plate may be attached or couple the pants 1700.

Figure 17C:
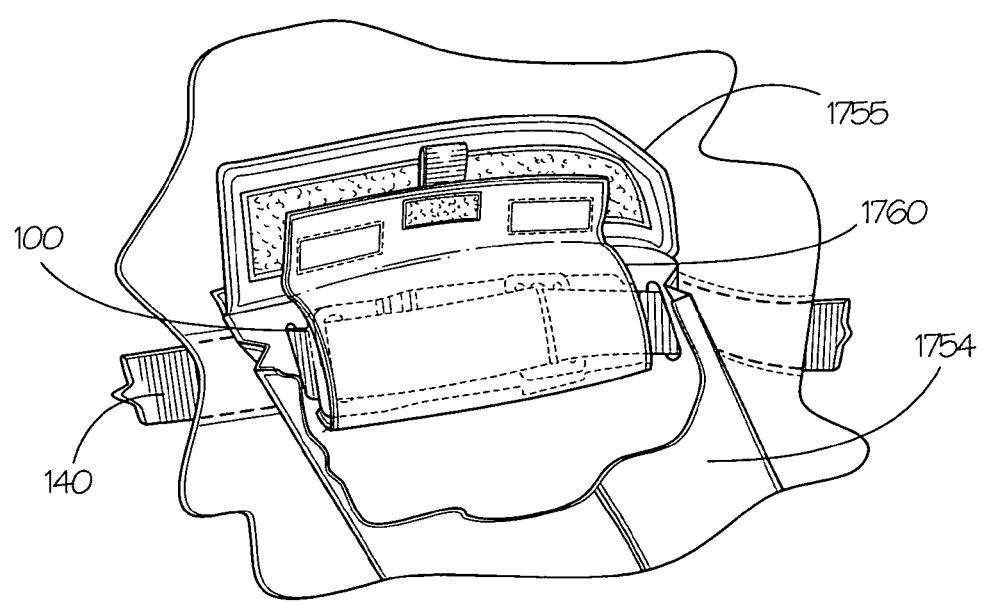
FIG. 17C illustrates an exemplary embodiment of a tourniquet system incorporated into a second exemplary embodiment of a cargo-type pocket of a pair of pants, according to this invention.

In various exemplary, nonlimiting embodiments, as illustrated in FIG. 17C, each of the cargo-type pockets, as represented by cargo pocket 1754, includes an additional flap 1760 that extends over at least a portion of the tourniquet system 100 to cover at least a portion of the tourniquet system 100. In these exemplary embodiments, to access the tourniquet system 100 or 100', the flap 1755 is first lifted and the additional flap 1760 is then separated from the flap 1755 to access the tourniquet system 100 or 100'.

Figure 18:
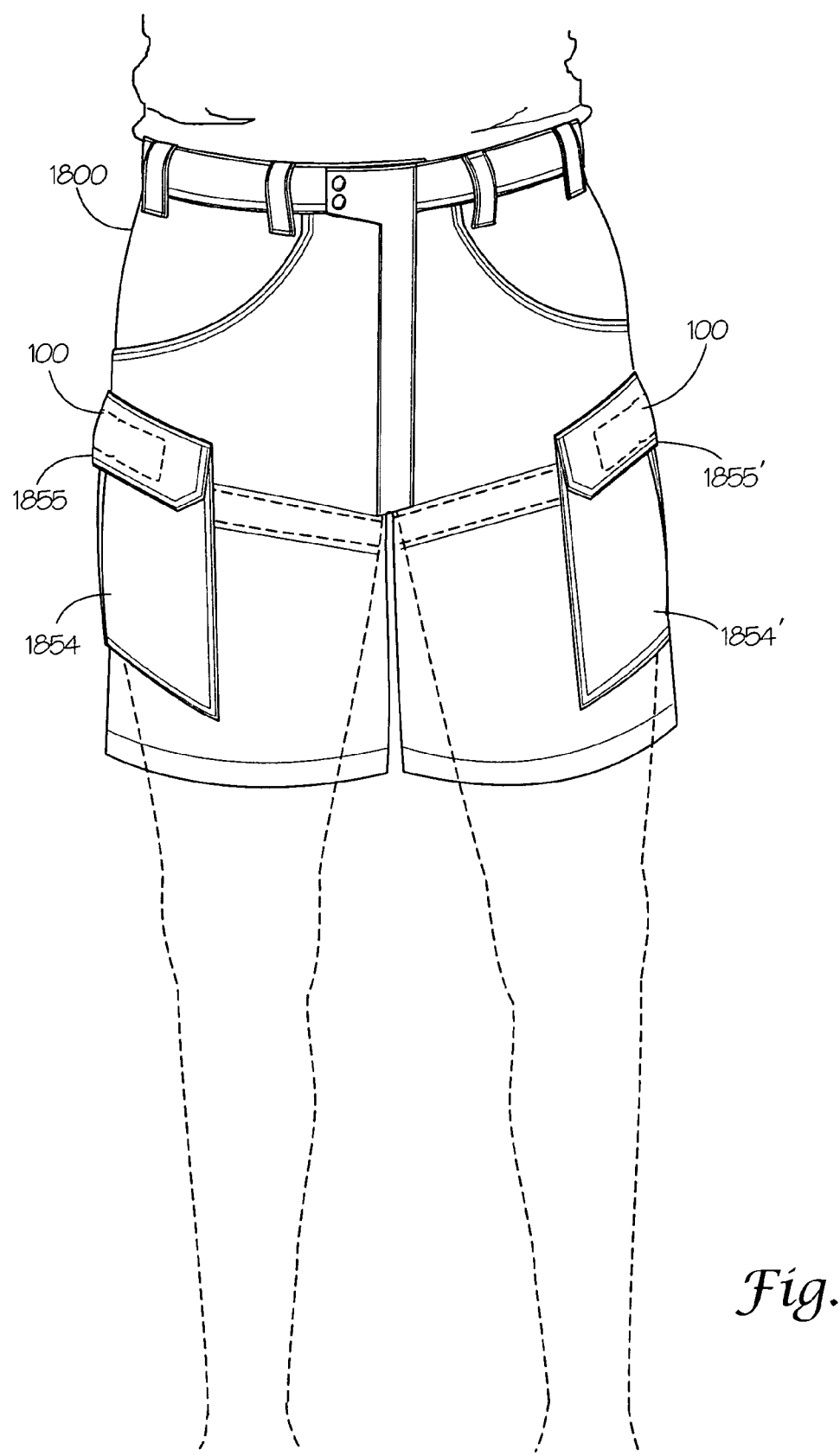
FIG. 18 illustrates an exemplary embodiment of a tourniquet system incorporated into a pair of shorts, according to this invention.

FIG. 18 illustrates an exemplary embodiment of a tourniquet system incorporated into a pair of shorts 1800, according to this invention. As shown in FIG. 18, the shorts 1800 include at least some of a first cargo pocket 1854 and a second cargo pocket 1854', each having a flap 1855 and 1855', respectively, for covering access to the interior of the respective cargo pockets 1854 and 1854'.

The flaps 1855 and 1855' act to cover and protect tourniquet systems 100 housed within the respective cargo pockets 1854 and 1854'.

It should be appreciated that the elements listed above as being included in the shorts 1800 correspond to and operate similarly to the cargo pockets 1754 and 1754', the flaps 1755 and 1755', and the tourniquet systems 100 housed within the respective cargo pockets 1754 and 1754'

Figure 19:
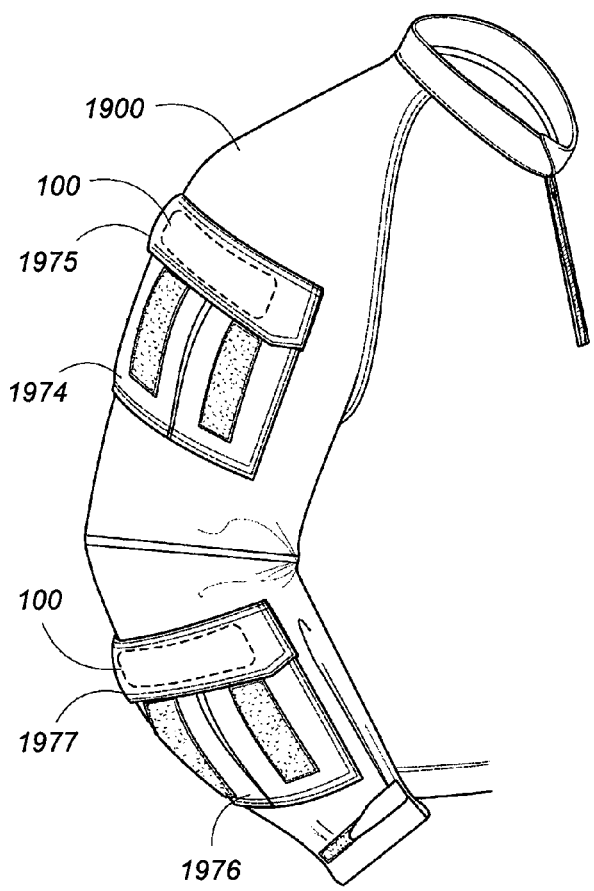
FIG. 19 illustrates an exemplary embodiment of a tourniquet system incorporated into a shirt, according to this invention.

FIG. 19 illustrates an exemplary embodiment of a tourniquet system incorporated into a shirt 1900, according to this invention. As shown in FIG. 19, the shirt 1900 include at least some of a first cargo pocket 1974 and a second cargo pocket 1976, each having a flap 1975 and 1977, respectively, for covering access to the interior of the respective cargo pockets 1974 and 1976.

The flaps 1975 and 1977 act to cover and protect tourniquet systems 100 housed within the respective cargo pockets 1974 and 1976.

It should be appreciated that the elements of the tourniquet systems 100 listed above as being included in the shirt 1900 correspond to and operate similarly to the tourniquet system 100 as included with the shirt 1200 of FIG. 12, while the cargo pockets 1254 and 1254' and the flaps 1255 and 1255' correspond to and operate similarly to the cargo pockets 1754 and 1756 and the flaps 1755 and 1757.

However, it should be understood that the size and positioning of the first cargo pocket 1974, the second cargo pocket 1976, the flap 1975, the flap 1977, and the tourniquet systems 100 included in the shirt 1900 is a design choice based upon the desired appearance and/or functionality of the particular shirt in which the tourniquet systems are incorporated or embedded.

Figure 20:
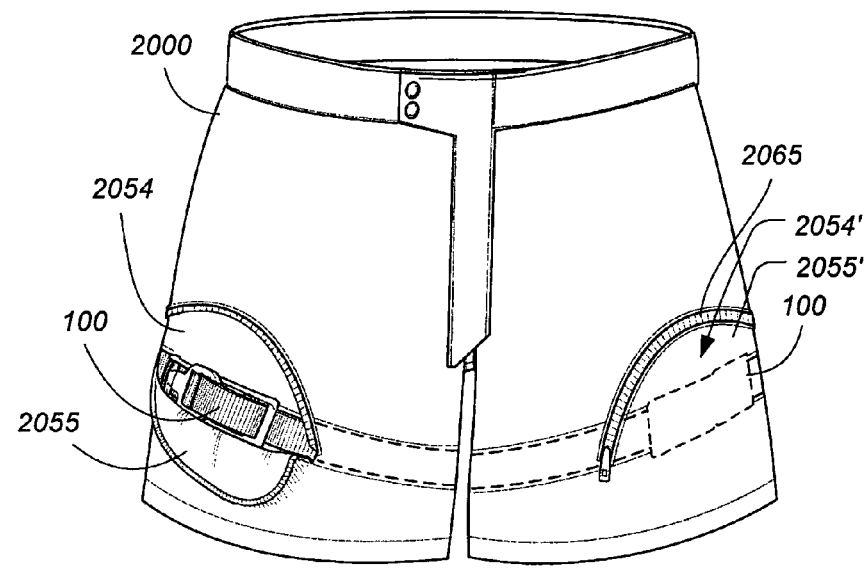
FIG. 20 illustrates an exemplary embodiment of a tourniquet system incorporated into a swimsuit, according to this invention.

FIG. 20 illustrates an exemplary embodiment of a tourniquet system incorporated into a swimsuit 2000, according to this invention.

As shown in FIG. 20, the swimsuit 2000 include at least some of a zippered access aperture 2054 and a second zippered access aperture 2054', each having a flap 2055 and 2055', respectively, for covering access to the interior of the respective zippered access apertures 2054 and 2054'.

The flaps 2055 and 2055' act to cover and protect tourniquet systems 100 housed within the respective zippered access apertures 2054 and 2054'.

It should be appreciated that the zipper 2065 may, as illustrated in FIG. 20, may form an arcuate or half-moon shape. Alternatively, the zipper 2065 may be formed in a straight or substantially straight line.

Figure 21:
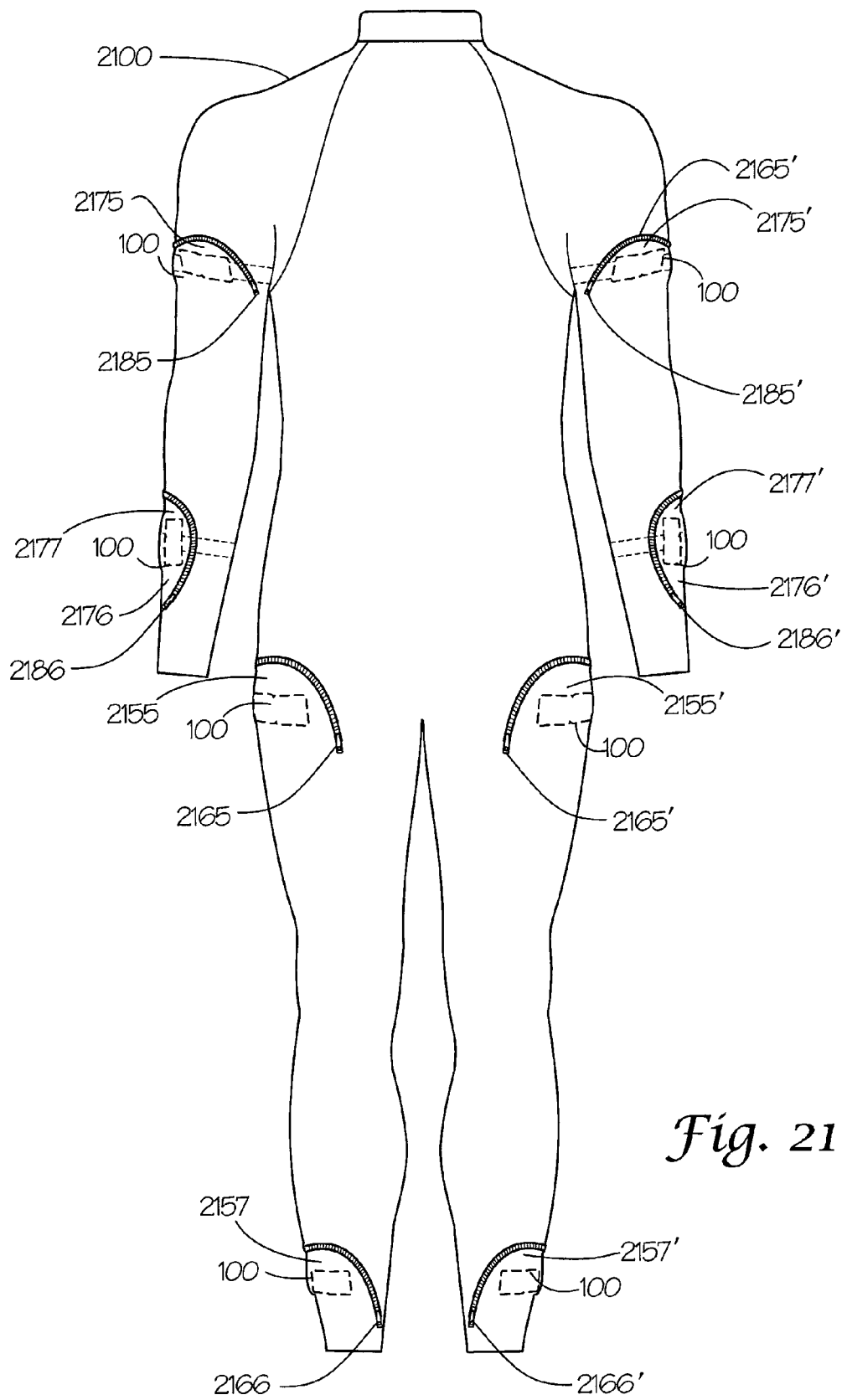
FIG. 21 illustrates an exemplary embodiment of a tourniquet system incorporated into a wetsuit, according to this invention.

FIG. 21 illustrates an exemplary embodiment of a tourniquet system incorporated into a wetsuit 2100, according to this invention.

As shown in FIG. 21, the wetsuit 2100 includes a plurality of zippered access apertures. Each zippered access aperture is covered by a flap 2175, 2175', 2177, 2177', 2155, 2155', 2157, and 2157', respectively. Each flap is releasably secured to cover its respective access aperture by a zipper 2185, 2185', 2186, 2186', 2165, 2165', 2166, 2166', respectively.

An appropriately sized tourniquet system 100 is housed beneath each zippered access aperture such that when a respective zipper is unzipped the flap can be moved away, exposing an embedded tourniquet system.

It should be appreciated that the number and placement of the embedded internal tourniquet systems and zippered access apertures is a design choice based upon the desired appearance and/or functionality of the wetsuit 2100. It should also be understood that the zippered access apertures and flaps may represent any type of sealable and/or resealable access aperture.

While this invention has been described in conjunction with the exemplary embodiments outlined above, it is evident that many alternatives, modifications, and variations will be apparent to those skilled in the art. Such adaptations and modifications should and are intended to be comprehended within the meaning and range of equivalents of the disclosed exemplary embodiments. It is to be understood that the phraseology of terminology employed herein is for the purpose of description and not of limitation. Accordingly, the foregoing description of the exemplary embodiments of the invention, as set forth above, are intended to be illustrative, not limiting. Various changes, modifications, and/or adaptations may be made without departing from the spirit and scope of this invention.

What is claimed is:

1. A tourniquet system embedded within a garment comprising:
 a band having a first end portion and a second end portion;
 a bar, wherein the bar comprises an elongate portion of material having at least a first band receiving aperture, a second band receiving aperture, and a third band receiving aperture formed therethrough, wherein each band receiving aperture is fully within the bar, and wherein the bar comprises at least one locking protrusion that extends from at least one of a first end portion or a second end portion of the bar; and
 an anti-pinch plate, wherein the anti-pinch plate includes one or more band receiving apertures formed so as to allow at least a portion of the band to pass therethrough, wherein the anti-pinch plate includes two or more locking notches formed substantially along an edge portion of the anti-pinch plate, wherein each locking notch allows at least a portion of the bar to be releasably secured to the anti-pinch plate;
 wherein at least a portion of the band passes through at least one of the band receiving apertures formed in the anti-pinch plate, thereby maintaining the position of the band relative to the anti-pinch plate, wherein at least a portion of the band passes through the first band receiving aperture formed in the bar, wherein at least two portions of the band pass through the second band receiving aperture formed in the bar, wherein at least a portion of the band passes through the third band receiving aperture formed in the bar, and wherein the anti-pinch plate is positioned at least partially beneath the bar; and
 wherein at least a portion of the band and a portion of the bar are embedded within the garment such that at least a portion of the band is maintained within a channel formed in at least a portion of the garment such that the band is maintained in a desired location relative to the garment;
 wherein the at least one locking protrusion comprises at least one substantially "T" shaped extension; and
 wherein each substantially "T" shaped extension is configured to interact with the two or more locking notches such that one side of each substantially "T" shaped extension interacts with a corresponding one of the at least two locking notches to releasably secure the bar to the anti-pinch plate.

2. The tourniquet system of claim 1, wherein at least a portion of the bar is accessible via a flap formed in the garment.

3. The tourniquet system of claim 1, wherein the garment comprises a pair of pants, a pair of shorts, a shirt, a jacket, a harness, a body-fitting framework, a wetsuit, a sky diving garment, a hazmat suit, a pressurized suit, a flight suit, or a uniform.

4. The tourniquet system of claim 1, wherein the bar is curved over its length.

5. The tourniquet system of claim 1, wherein at least one of the apertures formed in the bar is formed such that the received band is oriented in a manner parallel to a longitudinal axis of the bar.

6. The tourniquet system of claim 1, wherein at least one of the apertures formed in the bar is formed such that the received band is oriented in a manner perpendicular to a longitudinal axis of the bar.

7. The tourniquet system of claim 1, wherein the anti-pinch plate is curved over its length.

8. The tourniquet system of claim 1, wherein the two or more locking notches are formed by an edge portion of the anti-pinch plate.

9. The tourniquet system of claim 1, wherein the two or more locking notches comprise a cord or banding material that is attached or coupled to the anti-pinch plate.

10. The tourniquet system of claim 1, wherein the at least one locking protrusion is formed so as to be capable of interacting with the two or more locking notches to allow the bar to be releasably secured to the anti-pinch plate when the tourniquet system is not in use.

11. The tourniquet system of claim 1, wherein the anti-pinch plate is attached to the garment.

12. The tourniquet system of claim 1, wherein the tourniquet system is located proximate an upper portion of a leg portion of the garment.

13. The tourniquet system of claim 1, wherein the-tourniquet system is located proximate a lower portion of a leg portion of the garment.

14. The tourniquet system of claim 1, wherein the tourniquet system is located proximate an upper portion of an arm portion of the garment.

15. The tourniquet system of claim 1, wherein the tourniquet system is located proximate a lower portion of an arm portion of the garment.

16. The tourniquet system of claim 1, wherein the anti-pinch plate is attached or coupled to an exterior portion of the garment.

17. The tourniquet system of claim 1, wherein at least a portion of the band is maintained within the garment by a series of loops formed around at least a portion of a circumference of an inner surface of the garment.

18. The tourniquet system of claim 1, wherein the at least one locking protrusion extends from the first end portion of the bar and wherein a second locking protrusion extends from the second end portion of the bar.

19. The tourniquet system of claim 18, wherein the second locking protrusion comprises at least one substantially "T" shaped extension.

20. A tourniquet system comprising:
a band;
a bar having at least three apertures formed therethrough, wherein each aperture is fully within the bar, and wherein at least a portion of the band passes through each aperture, and wherein the bar comprises at least one locking protrusion that extends from at least one of a first end portion or a second end portion of the bar; and
an anti-pinch plate, wherein the anti-pinch plate includes two or more locking notches, wherein each locking notch allows at least a portion of the bar to be releasably secured to the anti-pinch plate, and wherein at least a portion of the bar is positioned above the anti-pinch plate;
wherein the anti-pinch plate is attached to a garment and wherein at least a portion of the band is maintained within a channel formed in at least a portion of the garment;
wherein the at least one locking protrusion comprises at least one substantially "T" shaped extension: and
wherein each substantially "T" shaped extension is configured to interact with the two or more locking notches such that one side of each substantially "T" shaped extension interacts with a corresponding one of the at least two locking notches to releasably secure the bar to the anti-pinch plate.

\* \* \* \* \*